US008263954B2

(12) United States Patent
Iwata

(10) Patent No.: US 8,263,954 B2
(45) Date of Patent: Sep. 11, 2012

(54) BOLUS, BOLUS MANUFACTURING METHOD, PARTICLE BEAM THERAPY SYSTEM, AND TREATMENT PLANNING APPARATUS

(75) Inventor: Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/126,235

(22) PCT Filed: Nov. 16, 2010

(86) PCT No.: PCT/JP2010/070363

§ 371 (c)(1),
(2), (4) Date: Apr. 27, 2011

(87) PCT Pub. No.: WO2012/066631

PCT Pub. Date: May 24, 2012

(65) Prior Publication Data

US 2012/0119105 A1 May 17, 2012

(51) Int. Cl.
*G21K 5/04* (2006.01)

(52) U.S. Cl. .................. 250/505.1; 250/492.3; 378/156; 378/159

(58) Field of Classification Search ............... 250/505.1, 250/492.3; 378/65, 145, 156, 159
See application file for complete search history.

(56) References Cited

U.S. PATENT DOCUMENTS 6,087,672 A * 7/2000 Matsuda et al. ........... 250/505.1
7,297,967 B2 * 11/2007 Yanagisawa et al. ....... 250/492.3
7,525,104 B2 * 4/2009 Harada ..................... 250/396 R
2008/0006776 A1 1/2008 Furukawa et al.
2008/0067401 A1 3/2008 Harada
2010/0074393 A1 3/2010 Thran et al.

FOREIGN PATENT DOCUMENTS

JP 60-063500 A 4/1985
JP 10-211292 A 8/1998
JP 10-255707 A 9/1998

(Continued)

OTHER PUBLICATIONS

International Search Report (PCT/ISA/210) issued on Jan. 11, 2011, by Japanese Patent Office as the International Searching Authority for International Application No. PCT/JP2010/070363.

(Continued)

*Primary Examiner* — Kiet T Nguyen

(74) *Attorney, Agent, or Firm* — Buchanan Ingersoll & Rooney PC

(57) ABSTRACT

The objective is to obtain a bolus, with which there can be formed an irradiation field that is accurately suited to the depth-direction shape of an irradiation subject, and a particle beam therapy system. An irradiation orbit of a particle beam is defined by a first slant with respect to a first axis that starts from a first reference point, that is perpendicular to a beam axis, and that includes the first reference point and by a second slant with respect to a second axis that is perpendicular to the beam axis and the first axis; the shape of a bolus is set in such a way that the path length, of a particle beam, within the bolus in each of the irradiation orbits defined for combinations within a predetermined range among combinations of the first slant and the second slant, compensates the path length from a body surface to a to-be-irradiated portion.

20 Claims, 8 Drawing Sheets

FOREIGN PATENT DOCUMENTS

| | | | |
|---|---|---|---|
| JP | 2001-346892 | A | 12/2001 |
| JP | 2006-166947 | A | 6/2006 |
| JP | 2006-212081 | A | 8/2006 |
| JP | 2007-054537 | A | 3/2007 |
| JP | 2010-511857 | A | 4/2010 |
| WO | WO 2006/082651 | A1 | 8/2006 |

OTHER PUBLICATIONS

Written Opinion (PCT/ISA/237) issued on Jan. 11, 2011, by Japanese Patent Office as the International Searching Authority for International Application No. PCT/JP2010/070363.

* cited by examiner (a)

(b)

(c)

BOLUS, BOLUS MANUFACTURING METHOD, PARTICLE BEAM THERAPY SYSTEM, AND TREATMENT PLANNING APPARATUS

TECHNICAL FIELD

The present invention relates to a bolus that is utilized in a particle beam therapy system utilizing a charged particle beam, in order to modulate the energy distribution of a charged particle beam in accordance with an irradiation subject, the manufacturing method therefor, a particle beam therapy system utilizing the bolus, and a treatment planning apparatus for determining the specification of the bolus.

BACKGROUND ART

In the particle beam therapy, therapy is implemented by irradiating a charged particle beam onto a diseased site, which is a therapy subject, so as to cause damage to diseased tissue; the particle beam therapy is one of the broad-sense radiation therapies. Among radiations, a charged particle beam such as a proton beam or a heavy ion beam is different from a conventional γ-ray or an X-ray in that the dose delivery thereof steeply becomes maximum in a position that is deep in a body. The peak of a dose delivery is referred to as a Bragg peak; the position (attainable depth) where it occurs is determined by the energy of a charged particle. That is because a charged particle gradually loses its energy as it passes through a substance and it delivers many doses when its kinetic energy becomes zero. Accordingly, in the particle beam therapy, by controlling energy distribution, not only the planar shape but also the depth-direction irradiation coverage can be controlled. Therefore, in order to deliver a sufficient dose to a diseased tissue while suppressing exposure of the peripheral tissues, there is required a particle beam therapy system that can appropriately control planar and depth-direction irradiation coverage (referred to as an irradiation field, hereinafter).

Among beam irradiation methods for a particle beam therapy system, in an irradiation method which is utilized often now and is referred to as a broad method, a thin beam supplied from an accelerator is enlarged and then is made to penetrate a collimator for forming a planar shape and a bolus for forming an energy distribution so that an irradiation field is formed (for example, refer to Patent Documents 1 through 4). In this situation, in the bolus, when a beam penetrates the bolus, the energy is attenuated in accordance with the penetration length (thickness); therefore, a thickness distribution is set in such a way as to compensate the depth distribution from the body surface of an irradiation subject. For example, when the distal plane of an irradiation subject is the setting reference, regarding a beam as a parallel light, the thickness of the bolus is set in such a way that the distal plane enters the bolus, or strictly speaking, in such a way that a constant thickness is obtained when the bolus is superimposed on the tissue ranging from the distal plane to the body surface. Alternatively, taking the spread from a point light source into consideration, the thickness of the bolus is set in such a way that a constant thickness is obtained, when the bolus which has been enlarged at a predetermined magnification in the planar direction is superimposed on the tissue.

PRIOR ART REFERENCE

[Patent Document]

[Patent Document 1] Japanese Patent Application Laid-Open No. 10-255707 (Paragraphs 0009 through 0020, FIGS. 1 and 5)

[Patent Document 2] Japanese Patent Application Laid-Open No. 2006-166947 (paragraphs 0015 to 0016, FIG. 1)

[Patent Document 3] National Publication of International Patent Application No. 2006-082651 (paragraphs 0012 to 0013, FIG. 4)

[Patent Document 4] Japanese Patent Application Laid-Open No. 2007-54537 (paragraph 0017, FIG. 1)

DISCLOSURE OF THE INVENTION

Problems to be Solved by the Invention

As described above, in the case of a conventional bolus, a thickness distribution is set only taking the parallel light of a particle beam or the spread from a point light source into consideration. However, even in the case of the broad method, when as disclosed in Patent Document 1 or 2, a beam is enlarged through scanning by means of an electromagnet, there are required respective electromagnets for two directions, e.g., an x-direction electromagnet and a y-direction electromagnet, in a plane perpendicular to the beam axis. Accordingly, the x-direction and y-direction spread starting points of an actual particle beam differ from each other. Thus, there has been a problem that in the case where the thickness of a bolus is set by taking the parallel light and the point light source into consideration but without considering the spreading manner that differs depending on the direction, there cannot be formed an irradiation field that is accurately suited to the depth-direction shape of an irradiation subject.

The present invention has been implemented in order to solve the foregoing problem; the objective thereof is to obtain a bolus, with which there can be formed an irradiation field that is accurately suited to the depth-direction shape of an irradiation subject, and a particle beam therapy system.

Means for Solving the Problems

A bolus according to the present invention is disposed in a particle beam therapy system and modulates energy distribution of a particle beam in accordance with a to-be-irradiated portion; the bolus is characterized in that on a beam axis of a charged particle beam that enters the bolus at the upstream side thereof, a first reference point and a second reference point, which is at the downstream side of the first reference point, are situated; an irradiation orbit of a particle beam that penetrates the bolus and reaches the to-be-irradiated portion is defined by a first slant from the beam axis with respect to a first axis that starts from the first reference point, that is perpendicular to the beam axis, and that includes the first reference point and by a second slant from the beam axis with respect to a second axis that is perpendicular to the beam axis and the first axis and includes the second reference point; and the shape of the bolus is set in such a way that the path length, of a particle beam, within the bolus, in each of the irradiation orbit defined for combinations within a predetermined range among combinations of the first slant and the second slant, compensates the path length from a body surface situated at the upstream side of the to-be-irradiated portion to the to-be-irradiated portion.

A bolus manufacturing method according to the present invention is characterized by including a step of acquiring inner-body depth data, which is the path length from the body surface to the to-be-irradiated portion, for each of combinations of the first slant and the second slant; a step of setting the shape of a bolus in such a way that the path length is obtained by compensating the acquired inner-body depth data; a step of creating bolus machining data, based on the set bolus shape; and a step of machining a bolus, based on the created machining data.

A particle beam therapy system according to the present invention is provided with an irradiation nozzle that scans a particle beam supplied from an accelerator by means of two electromagnets that range in the traveling direction of the particle beam and whose scanning directions are different from each other, and that irradiates the particle beam in such a way as to enlarge the irradiation field thereof; and the bolus disposed in a particle beam irradiated from the irradiation nozzle. The particle beam therapy system is characterized in that the bolus is disposed in such a way that the first axis for setting the shape of the bolus coincides with the scanning axis of the upstream electromagnet out of the two electromagnets and the second axis coincides with the scanning axis of the other electromagnet.

Moreover, a particle beam therapy system according to the present invention is provided with a three-dimensional data creation unit for creating three-dimensional data from image data of a body including the to-be-irradiated portion; an irradiation condition setting unit for setting an irradiation condition, based on the created three-dimensional data; and a bolus data creation unit for creating the shape data on the bolus in the particle beam therapy system, based on the set irradiation condition. The particle beam therapy system is characterized in that the three-dimensional data creation unit creates the three-dimensional data by utilizing at least the first slant obtained by means of scanning of the upstream electromagnet and the second slant obtained by means of scanning of said the other electromagnet.

Advantage of the Invention

In a bolus, a bolus manufacturing method, a particle beam therapy system, and a treatment planning apparatus according to the present invention, the shape of a bolus is set in accordance with the spreading manner, of a beam, that differs depending on the direction of the beam that penetrates the bolus and reaches an irradiation subject; therefore, there can be formed an irradiation field that is accurately suited to the depth-direction shape of the irradiation subject.

BEST MODE FOR CARRYING OUT THE INVENTION

Embodiment 1

Figure 1:
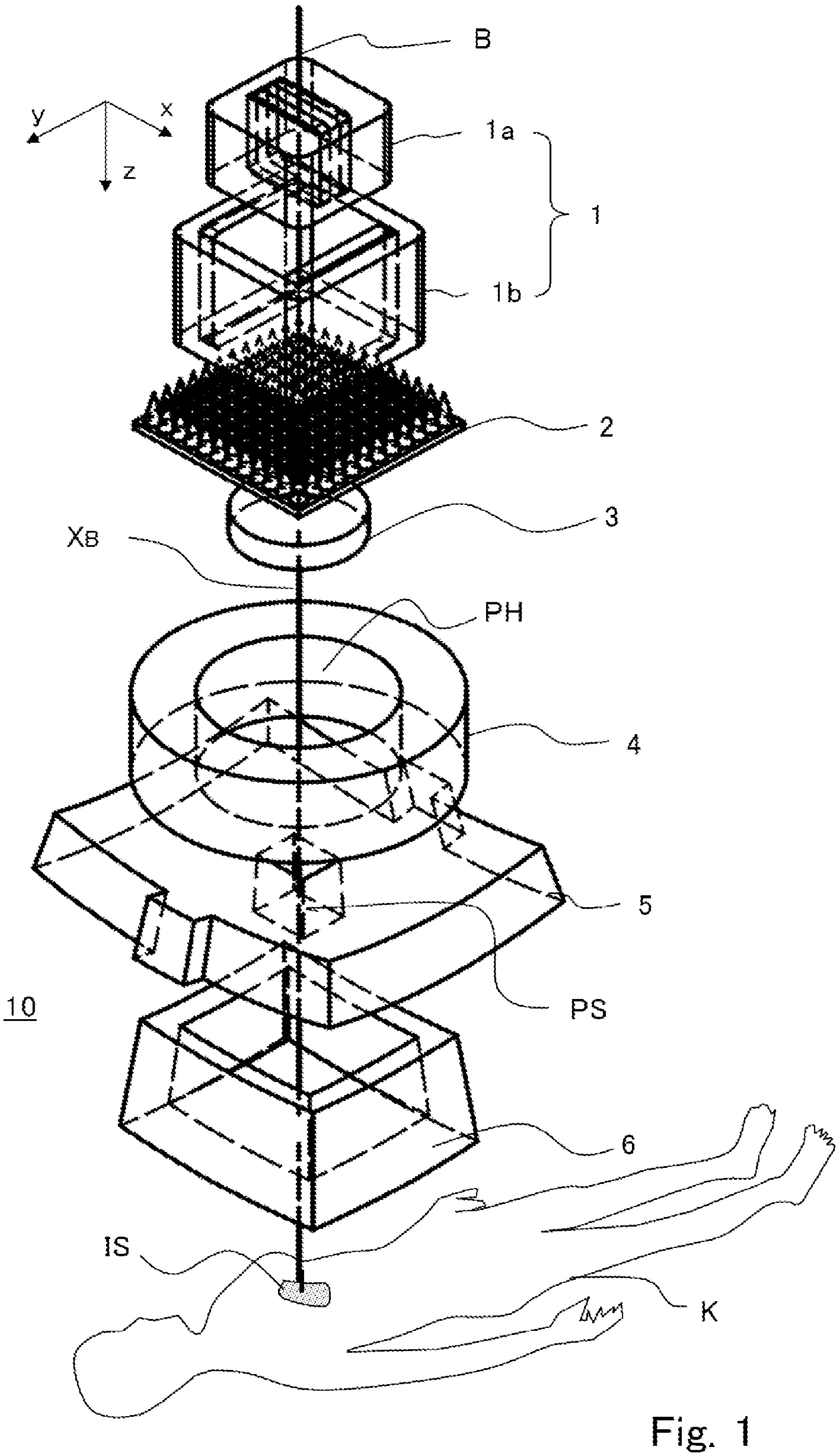
FIG. 1 is a view for explaining the configuration of an irradiation system, of a particle beam therapy system, that is provided with a bolus according to Embodiment 1 of the present invention.

The configurations of a bolus and a particle beam therapy system according to Embodiment 1 of the present invention will be explained below. FIGS. 1 through 5 are views and a flowchart for explaining the configurations of a bolus and a particle beam therapy system and a manufacturing method for the bolus according to Embodiment 1 of the present invention; FIG. 1 is a view illustrating the configuration of an irradiation system, of a particle beam therapy system, that is provided with a bolus.

Figure 2:
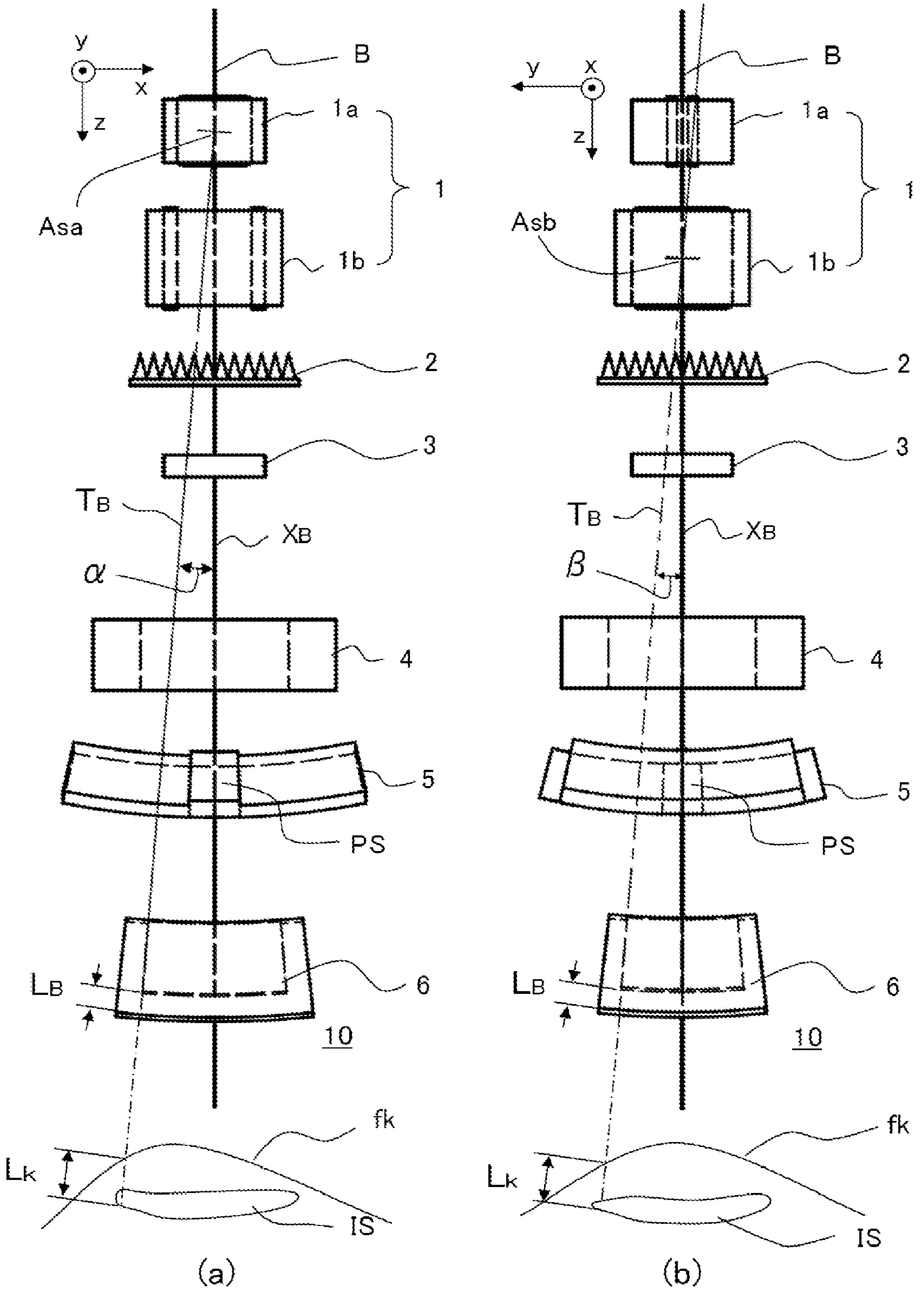
FIG. 2 is a set of views for explaining the configuration of an irradiation system, of a particle beam therapy system, that is provided with a bolus according to Embodiment 1 of the present invention, when the irradiation system is viewed from two directions that are perpendicular to each other with respect to the center of a beam.
Figure 3:
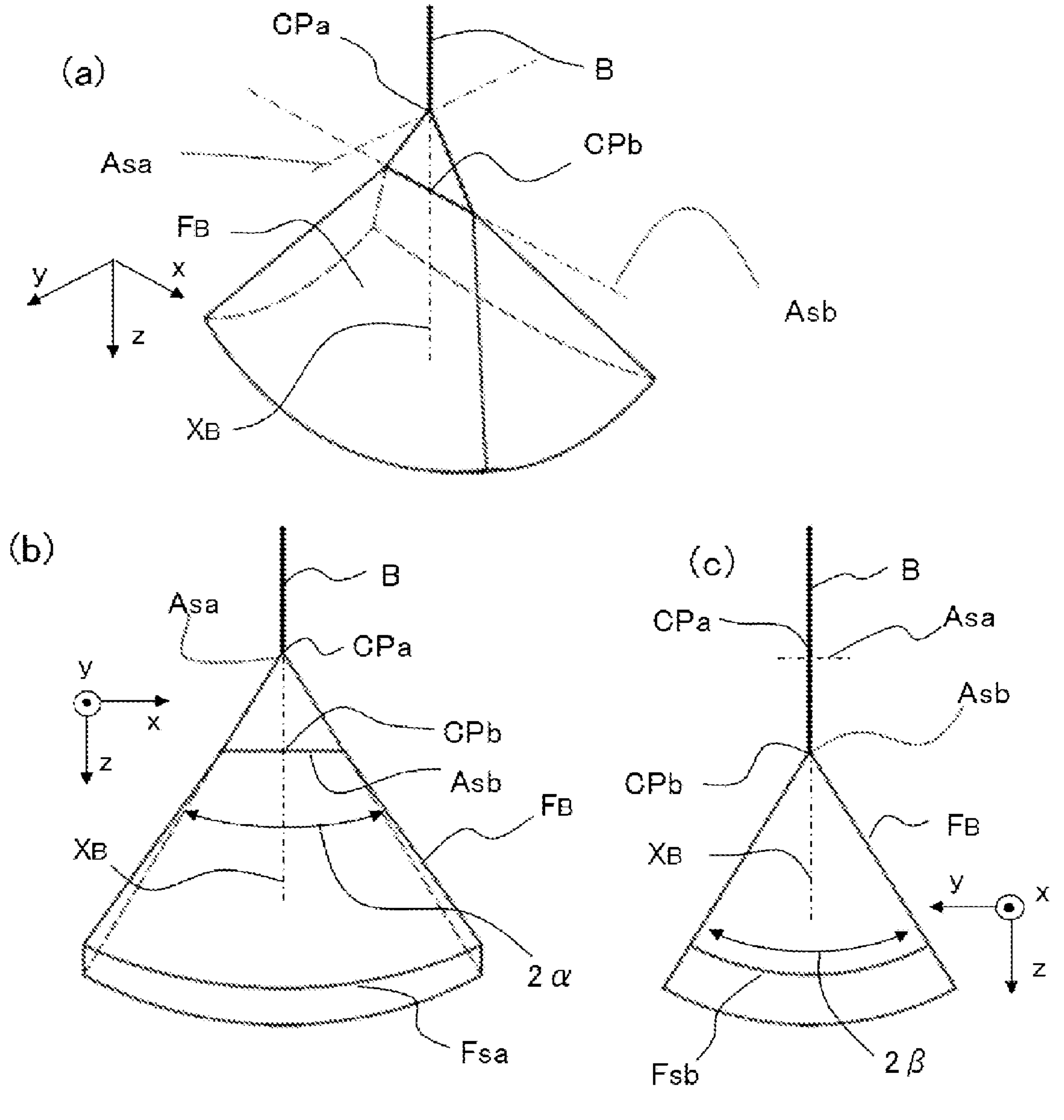
FIG. 3 is a set of views for explaining the beam-bundle state of a charged particle beam in an irradiation system of a particle beam therapy system according to Embodiment 1 of the present invention.
Figure 4:
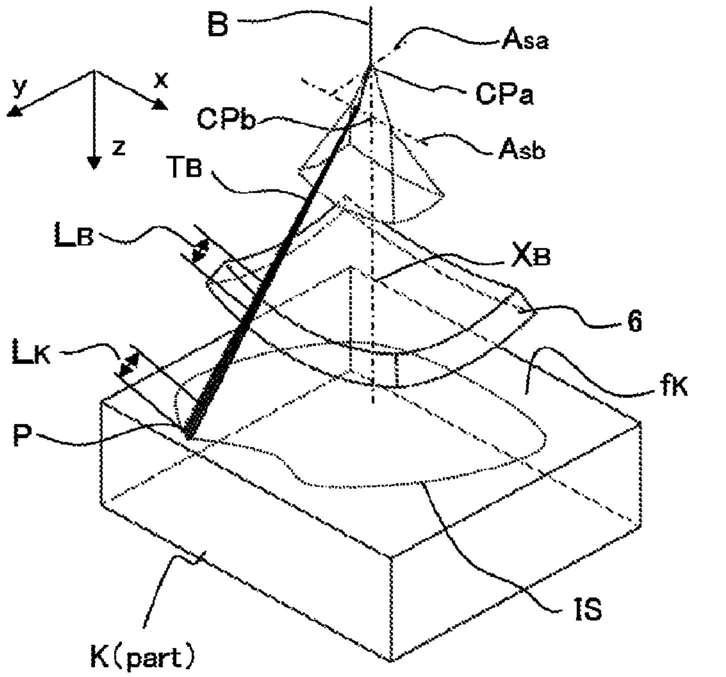
FIG. 4 is a set of views for explaining a bolus and the beam-bundle state of a charged particle beam in an irradiation system of a particle beam therapy system according to Embodiment 1 of the present invention.
Figure 4:
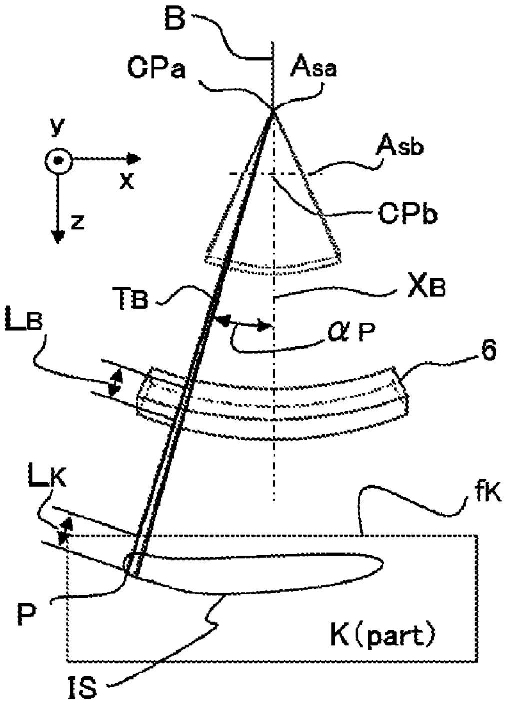
Figure 4:
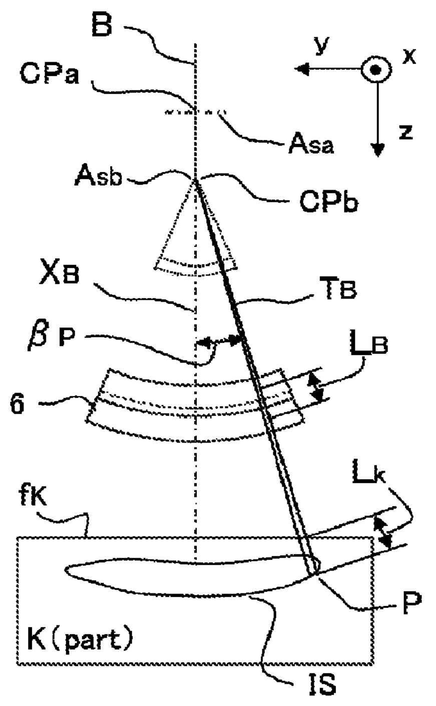
Figure 5:
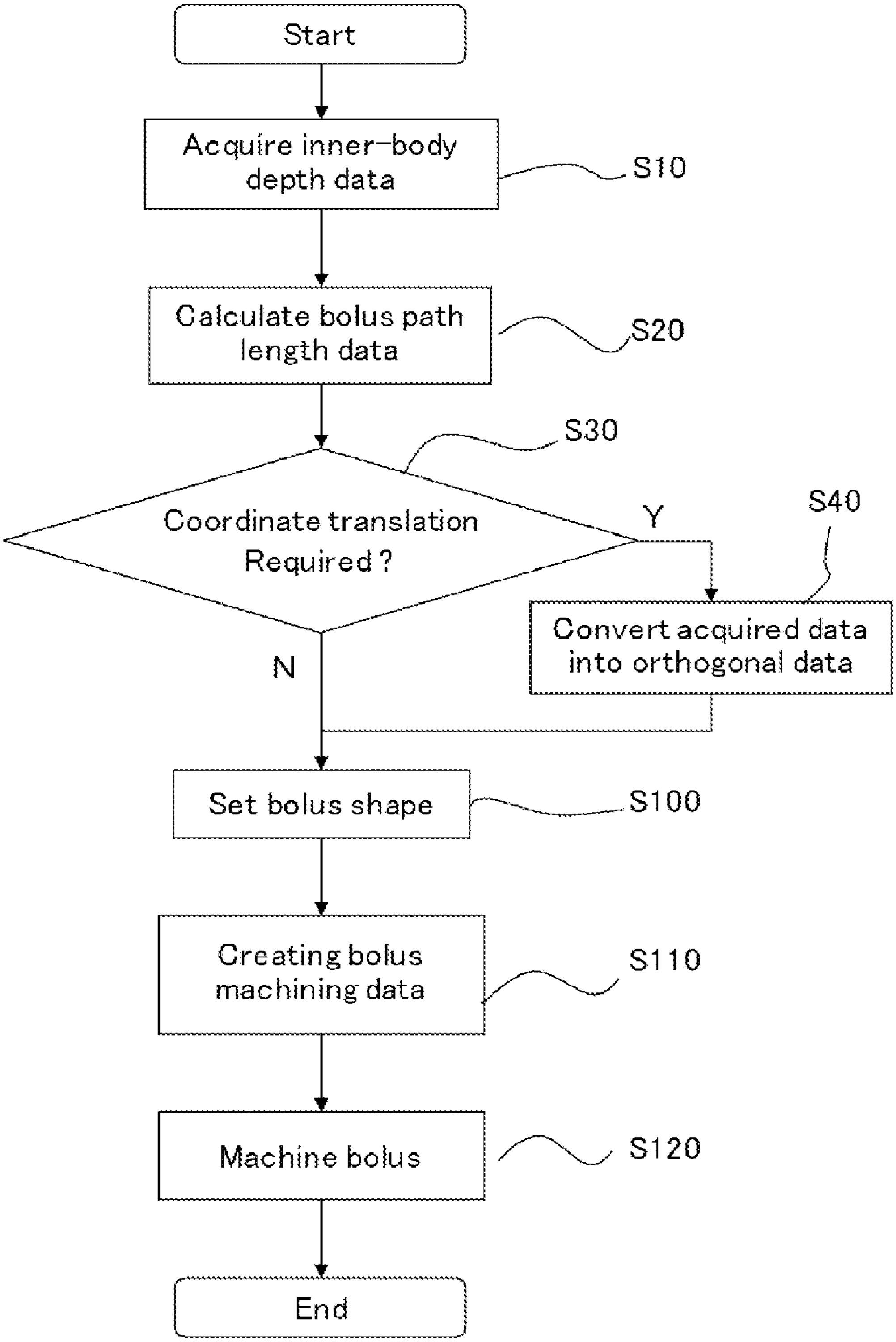
FIG. 5 is a flowchart for explaining a manufacturing method for a bolus according to Embodiment 1 of the present invention.

FIG. 2 is a set of views for illustrating the configurations of a particle beam therapy system and a bolus when they are viewed from directions that are perpendicular to each other with respect to the center (z direction) of a charged particle beam in FIG. 1; FIG. 2(*a*) is a side view when viewed from the y direction; FIG. 2(*b*) is a side view when viewed from the x direction. FIG. 3 explains the shape of a beam bundle in an irradiation system of a particle beam therapy system; FIG. 3(*a*) is a view illustrating the overall appearance of a beam bundle; FIGS. 3(*b*) and 3(*c*) are views when a beam bundle is viewed from directions that are perpendicular to each other with respect to the center (z direction) of a charged particle beam in FIG. 3(*a*); FIG. 3(*b*) is a side view when viewed from the y direction; FIG. 3(*c*) is a side view when viewed from the x direction. FIG. 4 extracts and illustrates a bolus in a beam bundle and a patient body including a diseased site, which is an irradiation subject, in order to explain about setting of the bolus in consideration of the spreading manner of a beam; FIG. 4(*a*) is a view illustrating the appearances of a bolus in a beam bundle and an irradiation subject; FIGS. 4(*b*) and 4(*c*) are views when a bolus and an irradiation subject are viewed from directions that are perpendicular to each other with respect to the center (z direction) of a charged particle beam in FIG. 4(*a*); FIG. 4(*b*) is a side view when viewed from the y direction; FIG. 4(*c*) is a side view when viewed from the x direction. FIG. 5 is a flowchart for explaining a manufacturing method for a bolus.

At first, as an assumption for a detailed explanation about the configuration of a bolus, there will be explained an irradiation system, including a bolus, for forming an irradiation field. As illustrated in FIGS. 1 and 2, a particle beam therapy system 10 is a system that processes a charged particle beam B supplied from an unillustrated accelerator, in accordance with a diseased site IS of a patient K as an irradiation subject, and to irradiate the charged particle beam B onto the diseased site. Accordingly, the particle beam therapy system 10 are provided with a wobbling electromagnet 1 (an upstream wobbling electromagnet 1*a*, a downstream wobbling electromagnet 1*b*) that functions as an irradiation nozzle for enlarging an irradiation field, by circularly scanning the charged particle beam B, which is supplied from the accelerator and has a so-called pencil-looking shape; a ridge filter 2 for enlarging the width of a Bragg peak in accordance with the thickness of the irradiation subject IS; a range shifter 3 for changing the energy (range) of the charged particle beam B in accordance with the depth (inner-body depth) of the irradiation subject IS from the body surface; a block collimator 4 for limiting the planar-direction (xy-direction) spread of an enlarged irradiation field to a predetermined area so as to prevent superfluous irradiation onto normal tissues; a multileaf collimator 5 that is configured with a plurality of leaf plates and leaf drive mechanisms for driving the respective leaf plates and limits an irradiation field in such a way that the planar-direction shape of the irradiation field coincides with the planar-direction shape of the irradiation subject IS; and a bolus 6 that limits the range of the charged particle beam B in such a way that the depth-direction (z-direction) shape of the irradiation field coincides with the depth-direction shape of the irradiation subject IS.

Next, there will be explained the operation and the principle of an irradiation system that enlarges an irradiation field by means of an irradiation nozzle in which the Wobbling method is utilized.

The charged particle beam B is accelerated by an unillustrated accelerator; then, as a so-called pencil beam having a diameter of approximately several millimeters, it is introduced to the irradiation system through a transport system. The charged particle beam B introduced to the irradiation system is scanned by the wobbling electromagnet 1 in such a way as to draw a circular orbit. As illustrated in FIG. 1 or 2, the wobbling electromagnet 1 is usually provided with an x-direction electromagnet 1*a* and a y-direction electromagnet 1*b*; the two electromagnets are arranged in series along the center axis $X_B$ of the charged particle beam B. Here, for clarity of description, the x direction and the y direction will be defined. In various specifications, coordinate systems are defined; however, in this "DESCRIPTION", the coordinate system is defined in the following manner. The direction in which the charged particle beam B travels is defined as the positive direction of the z axis. The x axis and the y axis are axes that are perpendicular to the z axis; the x axis and the y axis are also perpendicular to each other. Then, the xyz coordinate system is established in such a way as to be a right-handed coordinate system. In each of the examples in FIGS. 1 and 2, the upstream wobbling electromagnet 1*a* and the downstream wobbling electromagnet 1*b* scan a beam in the x direction and in the y direction, respectively. Due to the scanning by the electromagnets 1*a* and 1*b*, the irradiation field is expanded in the xy direction (planar direction).

The charged particle beam B whose irradiation field has been enlarged passes through the ridge filter 2. A ridge filter is formed, for example, in such a way that a great number of cones or plates whose cross sections are triangles are arranged on a plane; assuming that, for example, an irradiation field is divided into a great number of sub-areas, there exist beams that pass through different thickness from one another. For easier understanding, FIG. 1 or 2 illustrates cones that are arranged as in a pin holder ("kenzan"). In such a manner as described above, the width of a Bragg peak is spread out (SOBP: Spread-Out Bragg Peak). That is to say, the ridge filter 2 enlarges the irradiation field also in the z direction. Next, the charged particle beam B whose irradiation field has been enlarged passes through the range shifter 3. The range shifter 3 is a device that changes the energy of the charged particle beam B. Due to the range shifter 3, irradiation of the enlarged irradiation field can be performed onto a position of a desired inner-body depth. Next, the beam that has passed through the range shifter 3 passes through the block collimator 4. The block collimator 4 is, for example, a metal block in which a passing hole PH is provided, and limits the planar-direction (the xy plane) spread of the irradiation field. This is because superfluous irradiation onto normal tissues can be prevented by preliminarily limiting the irradiation coverage.

Next, the charged particle beam B passes through the multileaf collimator 5. Through a penetration shape PS formed based on the position of a plurality of leaves $\mathbf{5}_L$, the multileaf collimator 5 limits the shape of the irradiation field in the planar (xy) direction perpendicular to the beam axis $X_B$ in accordance with the shape of the diseased site IS, which is an irradiation subject. That is to say, the multileaf collimator 5 performs limitation and formation of the irradiation field in the xy direction. The multileaf collimator 5 is provided with at least the plurality of leaf plates $\mathbf{5}_L$ and a leaf drive mechanism $\mathbf{5}_D$ that drives the respective leaf plates $\mathbf{5}_L$. However, the configuration of the leaf drive mechanism $\mathbf{5}_D$ itself is not important, as long as the driving orbit of a leaf can be specified; when the leaf drive mechanism $\mathbf{5}_D$ itself is illustrated in the drawing, it is difficult to illustrate the structure of the leaf plate $\mathbf{5}_L$. Accordingly, for the sake of simplicity, in FIGS. 1 and 2 and the following drawings, there are illustrated only the leaf plate 5L and the formation in which the leaf plates 5L are integrated, which are extracted from the multileaf collimator 5.

Lastly, the charged particle beam B passes through the bolus 6. The bolus 6 is a limiter formed of resin or the like; it is formed in such a shape as to compensate the depth-direction shape of the diseased site IS, for example, the depth of the diseased site IS from the distal surface thereof. In this situation, the energy of the irradiation field is limited (formed in the z direction) to have a shape the same as the distal shape. That is to say, the bolus 6 performs limitation and formation of the irradiation field in the depth (z) direction. In addition, the distal surface signifies the surface of the deeper side of the diseased site IS as viewed from the body surface side; it is conceivable that in some cases, the depth of the proximal surface, which means the shallower side, is compensated, in contrast. There will be explained in detail the principle and operation in which the bolus 6 performs the depth-direction limitation and formation.

The function of the irradiation system of a particle beam therapy system is to form an irradiation field in accordance with the diseased site IS onto which a beam is irradiated. In the Wobbling method that is adopted, as the method therefor, in a particle beam therapy system according to Embodiment 1, a planar-direction irradiation field is enlarged only by the wobbling electromagnet 1. For example, the "large-area uniform irradiation method through spiral beam scanning" disclosed in Patent Document 1 is a specific example of this method, which is referred to as the "spiral wobbling method", among the Wobbling methods. Briefly speaking, the spiral wobbling method is to scan a beam (hereinafter, a beam dealt with not only in the particle beam therapy system but also in an ordinary apparatus is simply referred to as a "charged particle beam", and a beam utilized for explaining the radiation direction and the like of a charged particle beam is referred to as a "beam") in a spiral manner so as to enlarge an irradiation field; the scanning orbit (scanning locus) in the irradiation field is contrived so that the flatness is secured. Additionally, a beam scanning orbit according to the spiral wobbling method can be seen in FIG. 1 and the like of Patent Document 1.

Meanwhile, in general, the method which is referred to as the "Wobbling method" often signifies the "single-circle Wobbling method"; in that case, when an irradiation field is enlarged, the flatness is secured by means of a scatterer. Therefore, among the Wobbling methods, there exist not only a Wobbling method in which a scatterer is utilized but also a Wobbling method in which no scatterer is utilized; thus, the directional behavior of a beam differs depending on whether or not there exists a scatterer. In the case where a scatterer is utilized, the beam scanning angle for an irradiation field of a given size may be smaller than in the scanning method. Therefore, even in the case where as is the case in a conventional method, a bolus is created assuming that the beam is a parallel beam or a beam having a point-light-source spread, no significant problem is posed. In contrast, in the case where as the spiral wobbling method utilized in Embodiment 1, a beam is enlarged only by means of a scanning electromagnet without utilizing any scatterer, the irradiation direction of the beam that passes through a given point is a single direction that is determined mainly by the position thereof with respect to the scanning electromagnet.

FIG. 3 is a set of schematic diagrams illustrating the spreading manner (the shape of a beam bundle $F_B$) in which the charged particle beam B is enlarged by the couple of scanning electromagnets 1 in the irradiation system of the particle beam therapy system 10 according to Embodiment 1. Because the spiral wobbling method is utilized, the charged particle beam B is enlarged not in a point-light-source manner but in such a manner as illustrated in FIG. 3. For the sake of simplicity, the spreading manner of the charged particle beam, illustrated in FIG. 3, will be referred to as a "series-of-scanners spreading manner". In the case where a beam is enlarged not in a point-light-source manner but in a series-of-scanners spreading manner, a limiter suitable therefor needs to be designed.

The series-of-scanners spread will be explained in more detail hereinafter.

As illustrated in FIG. 3, the charged particle beam B is irradiated from the top to the bottom (in the z direction). Originally, the charged particle beam B is supplied as a thin beam, which is called a pencil beam. Reference points CPa and CPb are set on the beam axis $X_B$. The reference point CPa may be regarded as a position where the upstream wobbling electromagnet 1*a* (strictly speaking, a scanning axis $A_{Sa}$) is disposed; similarly, the reference point CPb may be regarded as a position where the downstream wobbling electromagnet 1*b* (strictly speaking, a scanning axis $A_{Sb}$) is disposed.

The upstream wobbling electromagnet 1*a* disposed at the reference point CPa scans the charged particle beam B with respect to the reference point CPa. The scanning direction, of the upstream wobbling electromagnet 1*a*, in which the charged particle beam B is scanned is on a plane (the xz plane) of FIG. 3(*b*) and passes through the reference point CPa on the beam axis $X_B$; the axis $A_{Sa}$, which is perpendicular to the beam axis $X_B$, is the action axis (scanning axis) of the upstream wobbling electromagnet 1*a*. The downstream wobbling electromagnet 1*b* disposed at the reference point CPb scans the charged particle beam B with respect to the reference point CPb. The scanning direction, of the downstream wobbling electromagnet 1*b*, in which the charged particle beam B is scanned is on a plane (the yz plane) of FIG. 3(*c*) and passes through the reference point CPb on the beam axis $X_B$; the axis $A_{Sb}$, which is perpendicular to the beam axis $X_B$ and the axis $A_{Sa}$, is the action axis (scanning axis) of the downstream wobbling electromagnet 1*b*. In other words, the scanning direction (x) of the upstream wobbling electromagnet 1*a* and the scanning direction (y) of the downstream wobbling electromagnet 1*b* are perpendicular to the beam axis $X_B$; the scanning direction (x) of the upstream wobbling electromagnet 1*a* and the scanning direction (y) of the downstream wobbling electromagnet 1*b* are perpendicular to each other.

Furthermore, the shape of the beam bundle $F_B$ will geometrically be explained with reference to FIG. 3.

As illustrated in FIG. 3(*b*), there is drawn a vertical (z-direction) line whose top end point is the reference point CPa, and then the reference point CPb is provided at a position other than the reference point CPa on the vertical line. There is obtained a sector Fsa through which the line passes when the line is pivoted by ±α° with respect to the reference point CPa. In the case where only the upstream wobbling electromagnet 1*a* is utilized, the sector Fsa corresponds to the spread of the charged particle beam B. Next, the sector Fsa is divided into the upper part and the lower part by the reference axis $A_{sb}$ that passes through the reference point CPb. There is obtained a region through which the lower part of the sector Fsa passes when the lower part of the sector Fsa is pivoted by ±β° with respect to the reference axis $A_{sb}$. This region is recognized as a sector Fsb in FIG. 3(*c*) and represents the spreading manner (the region through which the charged particle beam B can pass: the beam bundle $F_B$) of the charged particle beam B. That is to say, the shape of the beam bundle $F_B$ having a series-of-scanners spread is a sector whose x-direction and y-direction curvature radiuses are different from each other.

In order to explain the technical characteristics of a bolus corresponding to the spreading manner, of the charged particle beam B, which is created in accordance with the configuration of the foregoing irradiation system, the principle of a bolus will be explained at first.

As described in "Background Art", a charged particle beam is different from other radiations such as a γ-ray and an X-ray in that the dose delivery thereof steeply becomes maximal in a deep part of a body. The peak of the dose delivery is referred to as a "Bragg peak"; the position (attainable depth) where the Bragg peak occurs is determined by the energy of a charged particle. That is because a charged particle has a nature of gradually losing its kinetic energy as it passes through a substance and of delivering many doses when its kinetic energy becomes zero. In general, the accelerator, such as a synchrotron, of a particle beam therapy system accelerates a charged particle in such a way that it acquires certain energy. Accordingly, in the case where irradiation is directly performed without utilizing any limiter, a dose is delivered at an attainable depth corresponding to the energy accelerated by the accelerated. However, in practice, the shape of a diseased site, which is an irradiation subject, is three-dimensional and not constant in the depth direction. Thus, a bolus, which is a limiter, is utilized.

The relationship between the principle of the bolus and a conventional bolus manufacturing method will be explained.

A bolus is usually created by applying cutting processing to a resin block; while passing through the bolus, a charged particle beam loses its kinetic energy in accordance with the substance through which it passes, the density thereof, and the thickness thereof. In this situation, when comparison is made between substances having the same thickness, a substance having a larger atomic number causes more loss in the kinetic energy than a substance having a smaller atomic number. Additionally, as a result, even when a particle beam is irradiated in the air, it hardly loses its kinetic energy. For the sake of simplicity, it is assumed that the kinetic energy dissipated in the case where a charged particle beam passes through a resin by 1 cm is the same as the kinetic energy dissipated in the case where the charged particle beam passes through a human body by 1 cm. Moreover, it is assumed that the energy of a charged particle beam is adjusted in such a way that in the case where the charged particle beam, accelerated by an accelerator and then supplied, is directly irradiated, a Bragg peak is produced at a position that is 15 cm away from the body surface (the attainable depth is 15 cm).

For the sake of simplicity, it is assumed that a charged particle beam to be irradiated is a parallel beam. In the case where a bolus is disposed in the planar direction that is perpendicular to the incident direction of a charged particle beam, when the thickness of the end portion A, of the bolus, through which a charged particle beam enters is 3 cm, the attainable depth of the charged particle beam that penetrates the bolus becomes 12 cm (=15-3). When the thickness of the end portion B, of the bolus, through which a charged particle beam enters is 4 cm, the attainable depth of the charged particle beam that penetrates the bolus becomes 11 cm (=15-4). Accordingly, Bragg peaks are caused at a position that is 12 cm deep from the body surface immediately underneath the end portion A and at a position that is 11 cm deep from the body surface immediately underneath the end portion B. Thus, by letting $t_B(x, y)$ and $t_K(x, y)$ denote the thickness of a bolus at an arbitrary position (x, y) in the planar direction thereof and the depth of a desired irradiation portion immediately underneath of the bolus from the body surface, i.e., the thickness between the body surface and the desired irradiation portion, respectively, and by setting the thickness distribution of the bolus in such a way as to satisfy the equation (1), it is made possible that the energy of a charged particle beam can be emitted intensively on the surface of the desired irradiation portion of a diseased site, i.e., the surface of the desired irradiation portion can be damaged.

$$t_B(x,y)+t_K(x,y)=R \quad (1)$$

where R is the attainable depth of a particle beam that enters the bolus; under the above assumption, R is 15 cm.

In other words, the thickness distribution of a bolus is set in such a way as to compensate the depth distribution (the shape, simply speaking) from the body surface of a diseased site immediately underneath the bolus. Conventionally, with regard to the setting of the thickness, it is assumed that a charged particle beam is a parallel beam or a beam having a point-light-source spread; then, a bolus is manufactured. In addition, with regard to the setting of the thickness, in some cases, by regarding the body tissue as water, the thickness of a bolus is represented as the water-equivalent thickness obtained by converting the thickness of the bolus into the thickness equivalent to water; however, the foregoing manufacturing method applies also to this case.

In the bolus according to Embodiment 1 of the present invention, because the charged particle beam spreads in a series-of-scanners manner, a thickness distribution or, strictly speaking, the path-length distribution is set. More particularly, explanation will be made with reference to FIG. 4. In FIG. 4, the desired irradiation position P denotes the point at which the desired irradiation portion of the diseased site IS, which is an irradiation subject, is situated. For example, it is assumed that the desired irradiation position P is a point on the surface of the diseased site IS, deepest from the body surface $f_K$ of a patient body K. In the case where it is assumed that a beam spreads in a series-of-scanners manner, in order to make the beam reach the desired irradiation position P, an angle $\alpha_P$ at the reference point CPa and an angle $\beta_P$ on the action axis $A_{sb}$ are obtained; with respect to the action axis $A_{sa}$ that passes through the reference point CPa, the charged particle beam B is deflected by the angle $\alpha_P$ from the beam axis $X_B$, and with respect to the action axis $A_{sb}$ that passes through the reference point CPb, the charged particle beam B is deflected by the angle $\beta_P$ from the beam axis $X_B$.

The reason why the starting point of the angle $\alpha_P$ is not the action axis $A_{sa}$ but the reference point CPa is that because the charged particle beam B supplied from the accelerator 1 is pencil-like in shape, it can be regarded that all of it passes through the reference point CPa that is the intersection point of the action axis $A_{sa}$ with the beam axis $X_B$. The point, on the action axis $A_{sb}$, through which the charged particle beam B passes is uniquely determined by the scanning angle $\alpha_P$ with respect to the reference point CPa and the distance between the reference point CPa and the reference point CPb. As described above, under the assumption that a beam has a series-of-scanners spread (passing range), the polygonal line along which the beam reaches the desired irradiation position P, i.e., a "beam irradiation orbit $T_B$" can be drawn by defining it with the reference point CPa, the action axis $A_{sb}$, and the scanning angles $\alpha_P$ and $\beta_P$.

Before reaching the desired irradiation position P, the beam irradiation orbit $T_B$ penetrates the bolus 6 and the patient body K (at least from the body surface $f_k$ to the desired irradiation position P). The kinetic energy to be lost when the charged particle beam B penetrates the bolus 6 and the patient body K may be set to be the same as the energy that has been accelerated by the accelerator. That is to say, the bolus thickness, which determines the path length of the penetration, is set in such a way that the kinetic energy lost in the charged particle beam becomes the same as the accelerated energy. In this situation, the beam irradiation orbit $T_B$ is defined by the scanning angle α with respect to the reference point CPa and the scanning angle β with respect to the action axis $A_{sb}$ that passes through the reference point CPb located away from the reference point CPa. Then, when with regard to the path before the to-be-irradiated portion IS, $L_B$ denotes the penetration path length in the bolus 6, $L_K$ denotes the path length from the body surface $f_K$ to the to-be-irradiated portion IS, and as is the case in the equation (1), the energy of the charged particle beam B is represented by the attainable depth R, the shape of the bolus 6 may be set in such a way that the relationship among them in the equation (2) is satisfied.

$$L_B(\alpha,\beta)+L_K(\alpha,\beta)=R \quad (2)$$

In other words, assuming that two reference points CPa and CPb are specified, the shape of the bolus is directly defined (set) by three parameters (coordinates) consisting of the scanning angles α and β and the path length $L_B$. That is to say, strictly speaking, the shape of the bolus is defined not by the thickness distribution but by the path-length distribution. In this case, for example, in a region that is largely slanted from the beam axis $X_B$, correction in the thickness t cannot simply be performed by the angle of the slant. However, by defining it with (α, β, L) coordinates, the shape of the bolus can accurately be defined. Moreover, in the case where when a bolus is formed by applying cutting processing to a plate material, the machine that performs the cutting processing can change the direction of the rotation axle thereof, the direction of the rotation axle is defined by the scanning angles α and β and the cutting depth is defined by a simple conversion value obtained by applying four arithmetic operations to the path length $L_B$, so that processing data for the bolus can directly be created.

In contrast, in the case where even when the shape of the bolus is defined by the thickness distribution, the shape does not change compared with the path-length distribution, it is not necessarily required to stick to the path-length distribution. In that case, when the shape of the bolus 6 is set, it may be allowed that the distribution of the path length $L_B$ in the bolus 6 from the reference point CPa is specified, and then the shape of the bolus 6 is set, for example, by converting the path-length distribution into the planar-direction thickness distribution, as (x, y, z) coordinates. By converting into the thickness distribution, even a conventional machining apparatus makes it possible to manufacture a bolus that realizes an accurate energy distribution in which the spread of a charged particle beam is taken into consideration. In addition, a specific example of coordinate transformation will be explained in the following embodiments.

As described above, in practice, the charged particle beam B supplied from the accelerator is made to enter the bolus 6 after the width of the Bragg peak and the attainable depth are adjusted by the ridge filter 2 and the range shifter 3; therefore, in this case, "accelerated energy" may be read as "energy at a time when the charged particle beam B enters the bolus 6".

In other words, as represented in FIG. 5, there are provided a process of acquiring the length $L_K(\alpha, \beta)$ of a body path, i.e., acquiring inner-body depth data (the step S10); a bolus shape setting process in which there is calculated path length data $L_B((\alpha, \beta)$ that compensates the acquired inner-body depth data $L_K(\alpha, \beta)$, i.e., that satisfies the equation (2)(the step S20), and in the case where coordinate transformation of the acquired data is required ([Y] at the step S30), the acquired data is converted into orthogonal data (the step S40) and as the thickness distribution, the shape of the bolus is set (the step S100), and in the case where the coordinate transformation is not required ([N] at the step S30), the shape of the bolus is set without changing the coordinates; a process of creating bolus machining data (the step S110), based on the set bolus shape; and a process of machining a bolus (the step S120), based on the created machining data. As a result, the foregoing bolus 6 can be obtained, whereby a Bragg peak can securely by caused at the desired irradiation position P.

Similarly, with regard to the multileaf collimator 5, the driving orbit and the shapes and the arrangement of the leaves may be set, as described above, by considering the shape of the beam bundle $F_B$ having a series-of-scanners beam spread that is caused by enlarging an irradiation field by means of two scanning electromagnets 1*a* and 1*b* whose scanning directions are different from each other.

As a method of enlarging an irradiation field, there has been explained a spiral wobbling method in which a scanning locus becomes a spiral; however, as explained in the following embodiments, another spiral wobbling method may be utilized, and the method may not be limited to a spiral wobbling method. Moreover, the electromagnet that functions as an irradiation nozzle is not limited to the wobbling electromagnet 1; it is only necessary that the irradiation nozzle is to enlarge an irradiation field by means of two electromagnets whose scanning directions are different from each other.

As described above, the bolus 6 according to Embodiment 1 is provided in the particle beam therapy system 10 and is to modulate the energy distribution of the particle beam B, which is the charged particle beam B, in accordance with the to-be-irradiated portion IS. The particle beam therapy system 10 is configured in such a way that on the beam axis $X_B$ of the charged particle beam B that enters the bolus 6 at the upstream side thereof, a first reference point CPa and a second reference point CPb, which is at the downstream side of the first reference point CPa, are situated; the irradiation orbit $T_B$ of the particle beam B that penetrates the bolus 6 and reaches the to-be-irradiated portion IS is defined by a first slant α from the beam axis $X_B$ with respect to a first axis $A_{sa}$ that starts from the first reference point CPa, that is perpendicular to the beam axis $X_B$, and that includes the first reference point CPa and by a second slant β from the beam axis $X_B$ with respect to a second axis $A_{sb}$ that is perpendicular to the beam axis $X_B$ and the first axis $A_{sa}$ and includes the second reference point CPb; and the shape of the bolus 6 is set in such a way that the path length $L_B$, of the particle beam B, within the bolus 6 in each of the irradiation orbits TB defined for combinations within a predetermined range and each have a numerical-value range, a resolution, and the like required to cover the to-be-irradiated portion IS, among combinations of the first slant α and the second slant β, compensates the path length $L_K$ from the body surface $f_K$ situated at the upstream side of the to-be-irradiated portion IS to the to-be-irradiated portion IS. As a result, even though the spreading manners differ from one another in the planar direction, there can be formed an irradiation field that is accurately suited to the depth-direction shape of the to-be-irradiated portion IS, which is an irradiation subject, in accordance with the spreading manner.

In particular, the shape of the bolus 6 is set in such a way that the relationship represented in "$L_B(\alpha, \beta)+L_K(\alpha, \beta)=R$" is satisfied: where α denotes the first slant, β denotes the second slant, $L_B(\alpha, \beta)$ denotes the path length, of a particle beam B, within the bolus 6 in an irradiation orbit $T_B$ defined by a combination of the first slant α and the second slant β, $L_K(\alpha, \beta)$ denotes the path length from the body surface $f_k$ to the to-be-irradiated portion IS in the irradiation orbit $T_B$ defined by the combination of the first slant α and the second slant β, and R denotes the attainable depth corresponding to the energy of a particle beam B that enters the bolus 6, respectively; therefore, the definition of the actual irradiation orbit TB and the bolus shape can be performed in the same coordinates system, and there can be formed a bolus that accurately compensates the depth distribution in the to-be-irradiated portion IS.

Moreover, the bolus manufacturing method according to Embodiment 1 of the present invention is configured in such a way as to include a process (S10) of acquiring inner-body depth data, which is the path length from the body surface $f_K$ to the to-be-irradiated portion IS, for each of the combinations of the first slant α and the second slant β; a process (S20 to S100) of setting the shape of a bolus in such a way that the path length is obtained by compensating the acquired inner-body depth data; a process (S110) of creating bolus machining data, based on the set bolus shape; and a process (S120) of machining a bolus, based on the created machining data. As a result, there can be obtained a bolus that can securely cause a Bragg peak at the desired irradiation position P.

Furthermore, the particle beam therapy system 10 according to Embodiment 1 of the present invention is configured in such a way as to be provided with the irradiation nozzle 1 that scans the particle beam B with two electromagnets 1*a* and 1*b* that range in the traveling direction of the particle beam B supplied from an accelerator and whose scanning directions are different from each other, and that irradiates the particle beam B in such a way as to enlarge the irradiation field and with the bolus 6 disposed in the particle beam B irradiated from the irradiation nozzle 1, and configured in such a way that the bolus 6 is disposed in such a way that the first axis for setting the shape of the bolus 6 coincides with the scanning axis $A_{sa}$ of the upstream electromagnet 1*a* out of two electromagnets and the second axis coincides with the scanning axis $A_{sb}$ of the other electromagnet 1*b*; therefore, even though due to the series-of-scanners spread, the spreading manners differ from one another in the planar direction, there can be formed an irradiation field that is accurately suited to the depth-direction shape of the to-be-irradiated portion IS, which is an irradiation subject, in accurate accordance with the spreading manner.

Embodiment 2

In Embodiment 1, there has been described the application of a bolus according to the present invention to the spiral wobbling method in which a beam is scanned in a spiral manner. However, the technical idea of the present invention is not limited to the foregoing scanning orbit shape (scanning locus) in the irradiation field of a beam; the effect of the present invention is demonstrated even in the case of other beam scanning loci, as long as the spreading manner is a series-of-scanners manner. Thus, in Embodiment 2, there will be described a case where a bolus according to the present invention is applied to an irradiation system having another typical beam scanning locus.

At first, there will be explained a beam scanning locus produced through the spiral wobbling method utilized in Embodiment 1. As disclosed in Patent Document 1, the spiral scanning locus is given by the equation (3) including the following three equalities.

$$r(t) = \sqrt{\frac{R_{max} - R_{min}}{\pi N} v_0 t + R_{min}^2} \tag{3}$$

$$\omega(t) = \frac{v_0}{\sqrt{\frac{R_{max} - R_{min}}{\pi N} v_0 t + R_{min}^2}}$$

$$\therefore \theta(t) = \theta(0) + \int_0^t \omega(\tau) d\tau$$

where $R_{min}$ is the radius at a time when the time t=0, $R_{max}$ is the radius at a time when the time t=T, and N is the scanning rotation speed. In addition, r(t) is the radial-direction coordinates, and θ(t) is the angle-direction coordinates; r(t) and θ(t) are represented through a polar coordinate system.

The shape of the beam scanning locus given by the equation (3) is spiral; the shape is effective in obtaining a uniform dose distribution by scanning a beam within a circular region. However, it is not required that in order to obtain a uniform dose distribution, the beam scanning locus is limited to a spiral locus. It is conceivable that the beam scanning loci for obtaining a uniform dose distribution through scanning by two electromagnets can be categorized into a number of typical patterns.

The Wobbling method is to form a uniform dose distribution by continuously scanning a beam. That is to say, it is desirable that the beam scanning locus in the Wobbling method is continuous and periodical. Thus, there has been studied a pattern in which a beam orbit is represented by a polar coordinate system and r(t) and θ(t) are continuously and periodically changed.

<Typical Pattern-1>

In the first pattern, r(t) and θ(t) are each defined as a function that changes continuously and periodically, as described below.

r(t)=continuous and periodical function (period $T_1$)

θ(t)=continuous and periodical function (period $T_2$)

In this situation, the respective periods of r(t) and θ(t), which are different from each other, may be utilized. Attention should be drawn to the fact that as for the angle θ, 360° can be regarded as 0° as it rotates once. In other words, 360° continues to 0°. When represented in radian, 2π can be regarded as 0.

As an example that realizes the foregoing pattern, there is advanced the spiral scanning locus represented by the equation (4) including the following three equalities.

$$r(\tau)=r_1+r_2 \sin(\omega_r\tau+\phi_r)$$

$$\theta(\tau)=\omega_\theta\tau$$

$$\tau=\tau(t) \tag{4}$$

where τ(t) is the parameter of the equation (4) that is represented by utilizing a parameter, and is the function of the time. $\omega_r$ is the angular velocity that determines r(t), and the period of r(t) is $2\pi/\omega_r$. $\phi_r$ is the initial phase. $\omega_\theta$ is the angular velocity that determines θ(t), and the period of θ(t) is $2\pi/\omega_\theta$.

Figure 6:
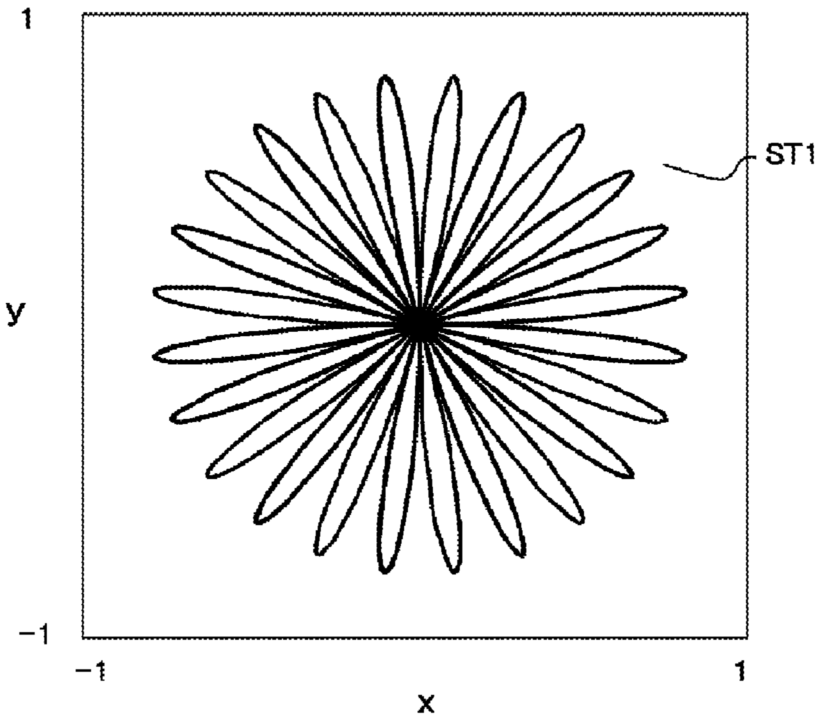
FIG. 6 is a chart representing an example of beam scanning locus in a particle beam therapy system according to Embodiment 2 of the present invention.

FIG. 6 represents an example of beam scanning locus STI created according to the equation (4). FIG. 6 represents a scanning locus on a given plane that is perpendicular to the beam axis; the abscissa denotes "x" and the ordinate denotes "y"; x and y are each normalized. The reason why in the equation (4), the parameter is not the time, is that it is required to make the drawing speed changeable depending on the place. For example, in FIG. 6, beam scanning concentrates in the vicinity of the center of the beam axis represented as the coordinates (0, 0); thus, in a portion in the vicinity of the center portion where the locus concentrates, contrivance such as raising the scanning speed is made so that a uniform dose distribution is obtained.

<Typical Pattern-2>

Figure 7:
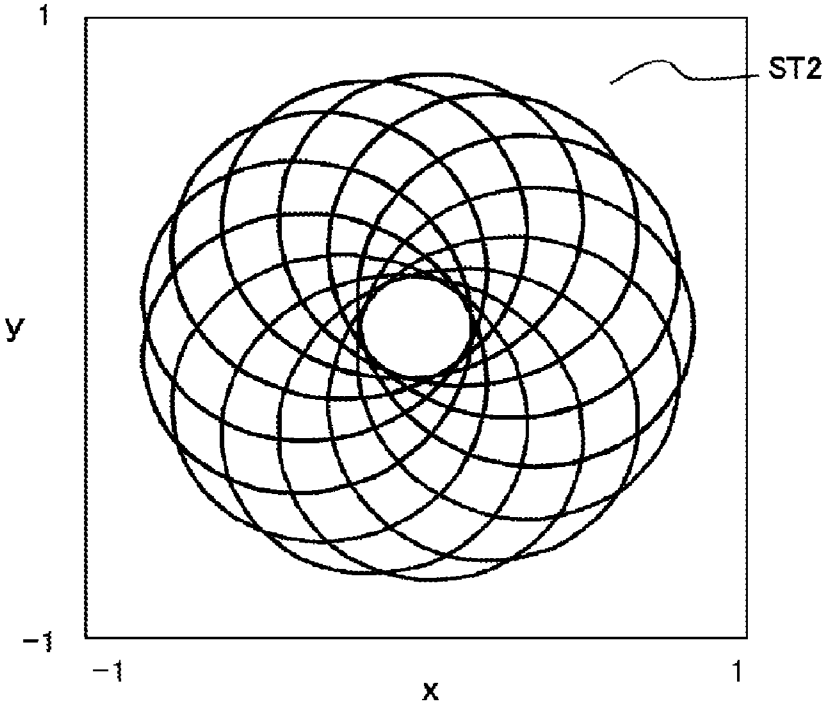
FIG. 7 is a chart representing another example of beam scanning locus in a particle beam therapy system according to Embodiment 2 of the present invention.

In the second pattern, two or more functions for defining a drawing pattern are combined so that a beam scanning locus is formed. For example, a function for drawing a large circle is combined with a function for drawing a small circle. An example is represented by the equation (5) including the following three equalities.

$$x(\tau)+r_1 \cos(\omega_1\tau+\phi_1)+r_2 \cos(\omega_2\tau+\phi_2)$$

$$y(\tau)=r_1 \sin(\omega_1\tau+\phi_1)+r_2 \sin(\omega_2\tau+\phi_2)$$

$$\tau=\tau(t) \tag{5}$$

where x(τ) and y(τ) are the x coordinate and the y coordinate, respectively, of a beam scanning locus; they are represented by use of an orthogonal coordinates system. FIG. 7 represents an example of beam scanning locus created according to the equation (5). As is the case with FIG. 6, FIG. 7 represents a scanning locus on a given plane that is perpendicular to the beam axis; the abscissa denotes "x" and the ordinate denotes "y"; x and y are each normalized.

Among toys, there exists a tool in which a gear-shaped disk is disposed in a circular hole inside of which teeth are formed; a geometrical pattern is drawn by inserting a pen tip into a small hole provided at a predetermined position in the disk and rolling the disk along the circular hole. A geometrical pattern created with the tool also belongs to this category. A curve drawn with this tool is referred to as a hypotrochoid; geometrically, the curve is defined as a locus drawn by a fixed point that is lr away from the center of a circle of a radius r when the circle of a radius r rolls without sliding along the inner circumference of a circle of a radius kr. In many mixing devices, the curve is adopted as the driving pattern for a mixing unit. The reason why the parameter is not the time t is that it is required to make the drawing speed changeable depending on the place, as is the case with the above example.

As described above, in the method in which through a wobbling electromagnet, a continuous and periodical pattern (line drawing) is drawn, the pattern is not necessarily a spiral. However, the idea in which by utilizing no scatterer but by contriving a beam orbit, large-area uniform irradiation is realized originates in the "spiral wobbling method"; therefore, in some cases, each of these methods described in Embodiment 2 is also referred to as a broad-sense spiral wobbling method. In addition, also in these broad-sense spiral wobbling methods, a beam spreads not in a point-light-source manner but in a series-of-scanners manner.

In other words, also in the particle beam therapy system having an irradiation system utilizing the broad-sense spiral wobbling method according to Embodiment 2, by utilizing the bolus 6 described in Embodiment 1, the energy attenuation distribution of a particle beam that penetrates the bolus 6 can be set in such a way that the depth distribution of an irradiation subject corresponding to the spread of the beam bundle $F_B$ of the charged particle beam B is compensated. Accordingly, it is made possible that based on the geometrical arrangement of the electromagnets, there is accurately formed an irradiation field that is suitable for the depth-direction shape of an irradiation subject. As a result, a difference, in the compensation accuracy, that is caused when a couple of electromagnets are utilized is eliminated, whereby a high-accuracy irradiation field can be formed.

Embodiment 3

In each of Embodiments 1 and 2, there has been described a case where a bolus is applied to irradiation through the Wobbling method. However, as described above, the irradiation method itself is not essential and does not confine the technical idea of the present invention. With regard to a particle beam therapy system, there has been proposed a spot-scanning method in which a charged particle beam is scanned by means of a couple of scanning electromagnets, and a spot is irradiated onto an irradiation subject in a pointillism manner. Also in the spot-scanning method, a beam spreads in a series-of-scanners manner. Therefore, in the case where a bolus is utilized in spot scanning, there is demonstrated an effect that the foregoing high-accuracy irradiation field can be formed.

Embodiment 4

In Embodiment 3, there has been described the application of a bolus according to the present invention to the spot-scanning method. There exists a raster-scanning method in which a charged particle beam is scanned by means of a couple of scanning electromagnets, as is the case with a spot-scanning method, and raster irradiation is performed onto an irradiation subject in a one-stroke writing manner. Also in the raster-scanning method, a beam spreads in a series-of-scanners manner. Therefore, in the case where a bolus is utilized in the raster-scanning method, the bolus according to the foregoing embodiment demonstrates an effect. In other words, also in the case where an irradiation field is enlarged through a scanning method such as a spot-scanning method or a raster-scanning method, when the bolus 6 according to the embodiment of the present invention is utilized, there is demonstrated an effect that the foregoing high-accuracy irradiation field can be formed.

Embodiment 5

There has been proposed a particle beam therapy system in which, for example, as disclosed in Patent Document 2, one of two scanning electromagnets is omitted, by contriving control method for a deflection electromagnet. However, even in the case of such an irradiation system, a deflection electromagnet for changing the orbit direction (that is not the irradiation orbit $T_B$ explained in each of Embodiments 1 through 4 but the direction of the beam axis itself) replaces the omitted scanning electromagnet that scans a charged particle beam; therefore, the beam bundle has a series-of-scanners spread, whereby a bolus according to each of the foregoing embodiments demonstrates an effect in forming a high-accuracy irradiation field.

Figure 8:
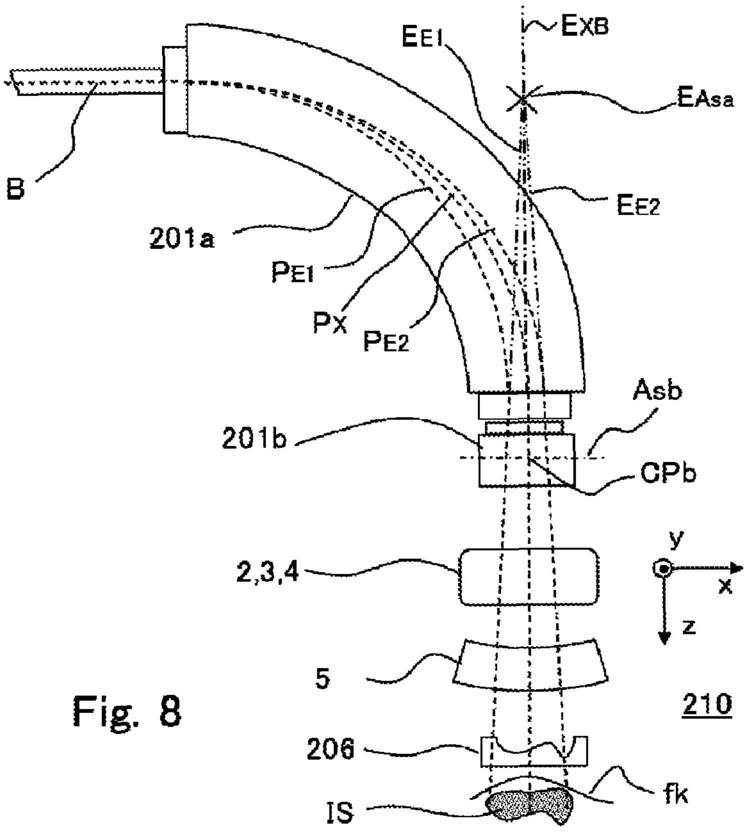
FIG. 8 is a view for explaining the configurations of a particle beam therapy system and a multileaf collimator according to Embodiment 5 of the present invention.

FIG. 8 is a view illustrating an irradiation system, in a particle beam therapy system, including a bolus 206 according to Embodiment 5. In FIG. 8, the beam axis of a charged particle beam B supplied in the horizontal direction (the x direction) is deflected to the vertical direction by a deflection electromagnet 201*a* and passes through a scanning electromagnet 201*b*; then, as is the case in Embodiment 1, the charged particle beam B is irradiated onto an irradiation subject, by way of a ridge filter 2, a range shifter 3, a ring collimator 4, a multileaf collimator 5, and the bolus 206. The configuration of a particle beam therapy system 210 according to Embodiment 5 is the same as that of a particle beam therapy system according to Embodiment 1, excluding the fact that instead of the scanning electromagnet 1*a* in the particle beam therapy system 10 according to Embodiment 1, the deflection electromagnet 201*a* is provided and that the setting reference of the shape (path-length distribution) of the bolus 206 is different.

In FIG. 8, inside the deflection electromagnet 201*a*, the charged particle beam B supplied in the horizontal direction is deflected in the z direction, while the beam axis $P_X$ draws an arc. In this situation, in the case of a normal deflection electromagnet, because control is performed in such a way that the magnetic field becomes constant, the beam bundle of the charged particle beam does not spread; however, by periodically changing the magnetic field, the deflection electromagnet 21 scans the charged particle beam B in the x direction so that the beam bundle can spread in the x direction from $P_{E1}$ to $P_{E2}$. In other words, the deflection electromagnet 201*a* plays the role of the upstream scanning electromagnet 1*a* of Embodiment 1. The portion thereafter is basically the same as the embodiment; the scanning electromagnet 201*b* further spreads the beam bundle, which has been spread in the x direction, in the y direction.

This beam spreading manner can be regarded as a spreading manner at a time when the scanning axis of the upstream scanning electromagnet 201*a* exists at an equivalent reference point $E_{AS}$ in FIG. 8 and a beam, irradiated from the upper side along the beam axis $E_x$, is scanned in the x direction (including the z-direction component) and spreads in the x direction from $E_{E1}$ to $E_{E2}$. Because inside the deflection electromagnet 201*a*, the beam axis is gradually deflected as the beam advances, the beam axes (=beam axis $E_{XB}$) at the entrance side and at the exit side are different from each other; thus, a scanning axis $E_{Asa}$ exists off the deflection electromagnet 201*a*. However, because the axis of a beam that enters the bolus 206 is the beam axis $E_{XB}$, the reference point CPa that specifies the position of the scanning axis $E_{Asa}$ can be regarded as existing on the beam axis of the beam that enters the bolus 206, as a manner of thinking; therefore, the scanning axis $E_{Asa}$ can be also regarded as being perpendicular to the beam axis $E_{XB}$ of the beam that enters the bolus 206. Accordingly, also in an irradiation system in which one of the electromagnets that perform scanning also plays the role of a deflection electromagnet, it may be allowed that the equivalent scanning axis $E_{Asa}$ is calculated based on the manner of beam spreading with respect to the beam axis $E_{XB}$ of the beam that enters a bolus, and as is the case in Embodiment 1, the path-length distribution in the bolus is set based on the equivalent scanning axis $E_{Asa}$ and the scanning axis $A_{sb}$ (the reference point CPb).

As can be seen from FIG. 8, in the case of an irradiation system in which one of the scanning electromagnets is omitted and instead of the omitted scanning electromagnet, the deflection electromagnet 201*a* that bends the orbit is utilized, the distance between the reference point (equivalent) CPa that specifies the equivalent scanning axis $E_{Asa}$ and the reference point CPb is wider than an ordinary irradiation system in which scanning is performed by an electromagnet dedicated to scanning (e.g., 1*a* and 1*b* in Embodiment 1). Accordingly, in the case of a bolus, a beam in which is assumed to spread in a point-light-source manner, there is more conspicuously posed a problem that the actual path differs from the calculated path. However, with regard to the shape of the bolus 206 according to Embodiment 5 of the present invention, the path length is set, taking the actual spread of a beam into consideration; therefore, a depth-direction irradiation field can accurately be formed.

As described above, the particle beam therapy system 210 according to Embodiment 5 is configured in such a way that one of the x-direction scanning and the y-direction scanning is performed by the deflection electromagnet 201*a* that deflects the direction of a beam axis, and by regarding that the beam axis for setting the reference points CPa and CPb passes through a point on the beam axis $E_{XB}$ of the charged particle beam B that enters the bolus 206, the shape and the position of the bolus 206 are set in such a way that the beam axis coincides with a first axis or a second axis; therefore, there is demonstrated an effect that a high-accurate irradiation field can be formed.

Embodiment 6

In each of Embodiments 1 through 5, there have been explained the configurations of a bolus and an irradiation system utilizing the bolus and the beam orbit in the irradiation system. In Embodiment 6, there will be explained a treatment planning apparatus in which with regard to a bolus and a particle beam therapy system according to each of the foregoing embodiments of the present invention, the operation condition and bolus manufacturing data are set.

Figure 9:
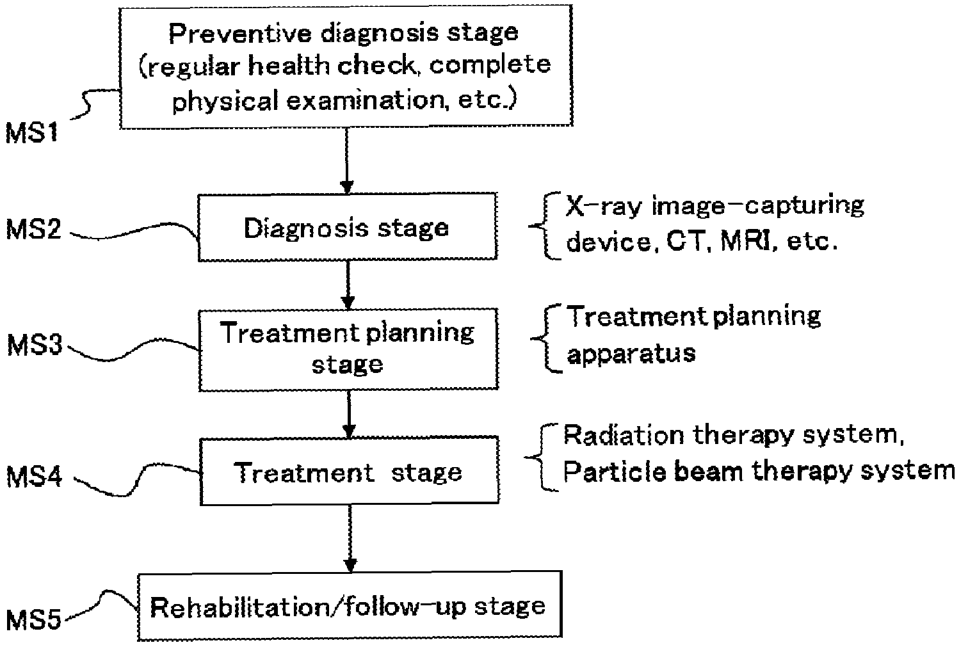
FIG. 9 is a diagram for explaining the flow of medical practice.

Here, before explaining a treatment planning apparatus, there will be explained medical practice on which a treatment plan to be implemented by the treatment planning apparatus is based. In general, it is conceivable that medical practice is configured with a number of stages. FIG. 9 represents the stages (flow) of medical practice by a flowchart and describes one or more apparatuses utilized in each stage. With reference to FIG. 9, the flow of a medical practice will be explained.

Specifically, medical practice may be roughly configured with a preventive diagnosis stage (MS1), a diagnosis stage (MS2), a treatment planning stage (MS3), a treatment stage (MS4), and a rehabilitation/follow-up stage (MS5). In particular, with regard to a particle beam therapy system, the respective apparatuses utilized in the foregoing stages are those described in the right column of FIG. 9. For example, the apparatuses utilized in the diagnosis stage (MS2) are an X-ray image-capturing device, a CT (Computed Tomography), an MRI (Magnetic Resonance Imaging); the apparatus utilized in the treatment planning stage (MS3) is the one that is called a treatment planning apparatus. In addition, the apparatuses utilized in the treatment stage (MS4) are a radiation therapy system and a particle beam therapy system.

Next, each of the stages will be explained.

The preventive diagnosis stage (MS1) denotes a stage where a diagnosis is implemented preventively, regardless of whether or not there has been shown the onset of a disease. For example, a regular health check and a complete physical examination fall into this stage; with regard to a cancer, a method utilizing fluoroscopic imaging such as radiology, a method utilizing tomography such as PET (Positron Emission Tomography) or PET/CT, and a method utilizing a genetic test (immunological test) are known.

The diagnosis stage (MS2) denotes a stage where a diagnosis to be followed by a treatment is implemented after the onset of a disease. In the case of particle beam therapy, in order to implement a treatment, three-dimensional information on the position and the shape of a diseased site is required. Accordingly, there are utilized various kinds of CT and MRI that are capable of obtaining three-dimensional data on a diseased site.

The treatment planning stage (MS3) denotes a stage where a treatment plan is created based on the result of the diagnosis. In the case of particle beam therapy, a treatment plan is created, in this stage, by a treatment planning apparatus according to Embodiment 6. The treatment planning apparatus will be explained in detail later; here, the residual stage will be explained.

The treatment stage (MS4) denotes a stage where an actual treatment is performed based on the result of the treatment plan. In the case of particle beam therapy, a particle beam therapy system is utilized in this stage. A bolus according to each of the foregoing embodiments is utilized for forming an irradiation field in the irradiation system of a particle beam therapy system. In addition, in some cases, the treatment stage is completed with a single irradiation; however, usually, there are implemented a plurality of irradiations, each irradiation of which is performed every certain period.

The rehabilitation/follow-up stage (MS5) literally denotes a stage where rehabilitation is performed or there is performed a follow-up to check whether or not a disease has recurred. In the case of a cancer, in a follow-up of this stage, as is the case in the preventive diagnosis stage, a method utilizing fluoroscopic imaging such as radiology, a method utilizing tomography such as PET or PET/CT, or a method utilizing a genetic test (immunological test) is adopted.

As described above, in medical practice, the treatment planning is a series of works performed after the diagnosis stage and before the treatment stage. In a particle beam therapy system, a charged particle beam is irradiated based on a treatment plan obtained through a treatment planning apparatus; therefore, a treatment planning apparatus in particle beam therapy is provided with units that approximately play the following roles.

Role A: a unit for creating three-dimensional data, based on a plurality of image information items for an irradiation subject, which are preliminarily obtained.

Role B: a unit for creating an optimum irradiation condition (treatment planning draft) under given requirements.

Role C: a unit for simulating and displaying a final dose distribution for the optimum result (treatment planning draft).

In other words, a treatment planning apparatus is provided with a role in which in response to the result of a diagnosis, irradiation condition required for treatment is set; furthermore, the treatment planning apparatus has a unit that plays a role of creating control data for the particle beam therapy system and the like, based on the set condition.

In order to play the foregoing roles, specifically, the treatment planning apparatus is provided with the following functions.

<Role A>

Function a: a function for creating three-dimensional data based on a tomographic image obtained in the diagnosis stage.

Function b: a function for displaying the created three-dimensional data as seen from various viewing points, as is the case with a three-dimensional CAD.

Function c: a function for distinguishing a diseased site from normal tissues and storing them in the created three-dimensional data.

<Role B>

Function d: a function for setting parameters for a particle beam therapy system utilized in the treatment stage and for simulating irradiation.

Function e: a function for optimizing irradiation under the requirements set by a user of the apparatus.

<Role C>

Function f: a function for displaying the optimized irradiation result in such a way as to be superimposed on the three-dimensional data.

<Role D>

Function g: a function for setting the shapes, of a multileaf collimator and a bolus, for realizing the optimized irradiation (including multi-port irradiation in the case where broad-beam irradiation is anticipated).

Function h: a function for setting the beam irradiation orbit for realizing the optimized irradiation (in the case where scanning irradiation is anticipated).

Function i: a function for creating a driving code, for a particle beam therapy system, for realizing the beam irradiation orbit.

<Others>

Function j: a function for storing various kinds data items created in the apparatus.

Function k: a function capable of reading various kinds of data items stored in the past and reusing past information.

There will be explained the system configuration of a treatment planning apparatus for realizing the foregoing functions. In recent years, almost no manufacturer of a treatment planning apparatus has designed and manufactured dedicated hardware; the hardware is configured based on a commercially available Unix (registered trademark) workstation or a PC, and as peripheral devices, universal devices are utilized in many cases. That is to say, manufacturers of treatment planning apparatuses primarily develop, manufacture, and sell treatment planning software. In the treatment planning software, for example, there is prepared a module for realizing the functions a through k, as a subprogram to be called by main program. By omitting, as may be necessary, the flow between the function a and the function k or re-implementing it by changing the requirements, the user of a treatment planning apparatus can create a treatment plan while calling necessary modules.

Next, while advancing the explanation to the functions or the modules for realizing those functions, there will be explained a treatment planning apparatus according to Embodiment 6.

Function a (module a) creates three-dimensional data based on a series of tomographic images obtained in the diagnosis stage. It is desirable that when a tomographic image is read, patient information such as a patient ID and scanning information (such as a slice distance, a slice thickness, FOV, and a tomographic condition) are also read in a corresponding manner. Here, the three-dimensional data denotes information required for virtually and three-dimensionally reproducing an imaging subject including a diseased site in a treatment planning apparatus. In general, there is utilized a method in which a virtual space is defined in a treatment planning apparatus, points are arranged within the virtual space in such a way as to be spaced evenly apart from one another and in a lattice-like manner, and the respective material information items, which are obtained from a tomographic image, are positioned at the corresponding points. The reason why Function a is required is that one of the biggest objects of a treatment planning apparatus is to simulate treatment, and for that purpose, it is necessary to reproduce a diseased site, which is an irradiation subject, and the peripheral tissues thereof.

Function b (module b) displays the created three-dimensional data as seen from various viewing points, as is the case with a three-dimensional CAD.

Function c (module c) distinguishes a diseased site from normal tissues and stores them in the created three-dimensional data. For example, it is assumed that a tomographic image is obtained through X-ray CT. In this case, the "material information" utilized in Function a corresponds to the radiolucency of an X-ray. That is to say, the three-dimensional model reproduced in the virtual space from this tomographic image represents the shape of a three-dimensional body formed of materials whose radiolucencies are different from one another. In the virtual space of a treatment planning apparatus, the "material information", i.e., the X-ray radiolucency is rendered by changing the color and the brightness. Furthermore, this "material information" makes it possible to understand that this part of the three-dimensional model reproduced in the virtual space corresponds to a bone or that part corresponds to a tumor, and a diseased site is distinguished from normal tissues. The result of the distinction between a diseased site and normal tissues can be stored in a storage device (such as a hard disk) of the treatment planning apparatus.

Function d (module d) sets parameters for a particle beam therapy system utilized in the treatment stage and simulates irradiation. The parameters for a particle beam therapy system denote geometric information on the particle beam therapy system and information on an irradiation field. The geometric information includes the position of the isocenter, the position of the bed, and the like. The information on an irradiation field includes the foregoing "coordinates of the reference point CPa and the coordinates of the reference point CPb" and the like. Additionally, the information on an irradiation field also includes the respective positions and the respective orientations of the bolus 6 or 206 (only 6 is described as a representative, hereinafter) from the reference point CPa and the reference point CPb.

Function e (module e) optimizes irradiation under the requirements set by a user of the treatment planning apparatus.

Function f (module f) displays the optimized irradiation result in such a way as to be superimposed on the three-dimensional data.

Function g (module g) sets the shapes, of the multileaf collimator 5 and the bolus 6, for realizing the optimized irradiation. This function is a one when broad-beam irradiation is anticipated, and includes a case of multi-port irradiation.

Function h (module h) sets the beam irradiation orbit for realizing the optimized irradiation. This function is a one when scanning such as spot scanning or raster scanning is anticipated.

Function I (module i) creates a driving code, for a particle beam therapy system, for realizing the beam irradiation orbit. In this situation, when as described later, a coordinate system conforming to a series-of-scanners spread is adopted and as described in Embodiment 1, the multileaf collimator 5 conforming to series-of-scanners is utilized, there can readily be created a driving code for realizing an opening shape (penetration shape SP) corresponding to the obtained optimum irradiation plan.

Function j (module j) stores various kinds of data items set and created in the apparatus.

Function k (module k) can read various kinds of data items stored in the past and reuse past information.

<Coordinate System Conforming Series-of-Scanners Spread>

In a conventional treatment planning apparatus, the three-dimensional data utilized in Function a and functions following to Function a are represented by an orthogonal coordinate system (xyz coordinate system). In the case of a multileaf collimator whose total shape is a conventional rectangular parallelepiped and a bolus whose shape is specified by the thickness distribution within a plane that is perpendicular to a beam axis, the arrangement direction thereof, the leaf driving direction, and bolus machining data (for example, NC data) are also represented by orthogonal-coordinate directions (for example, the x direction and the y direction); therefore, it is convenient to represent the three-dimensional data by an orthogonal coordinate system. That is because leaf driving data and shape data for creating the shape of the opening portion in such a way as to coincide with the shape of a diseased site coincide with each other or because bolus shape data and bolus machining data coincide with each other.

In contrast, in the case where the bolus 6 according to each of Embodiments of the present invention is manufactured in such a way that the depth distribution is faithfully compensated for the spread of a beam, the three-dimensional data cannot accurately be represented, in some cases, by the depth (machining depth) distribution in the direction of a plane that is perpendicular to the beam axis $X_B$, as described above. Accordingly, it is desirable to give the data for manufacturing a bolus, as an angle with respect to a reference point. That is to say, it is required to represent the shape data for manufacturing a bolus by machining a plate material, as a length corresponding to an angle with respect to a reference point, as explained in the equation (2).

Thus, the treatment planning apparatus according to Embodiment 6 of the present invention is configured in such a way that the three-dimensional data for a diseased site is represented by a special coordinate system.

Specifically, it is a special coordinate system represented by the following definition.

$$[\phi_a, \phi_b, r_b] \tag{D1}$$

where $\phi_a$ is a beam deflection angle (corresponding to $\alpha$ in the equation (2)) with respect to the reference axis (Asa) that is perpendicular to the beam axis $X_B$ and passes through the reference point CPa; $\phi_b$ is a beam deflection angle (corresponding to $\beta$ in the equation (2)) with respect to the reference axis ($A_{sb}$) that is perpendicular to the beam axis $X_B$ and the reference axis $A_{sa}$ and that passes through the reference point CPb; $r_b$ is a distance between the reference point CPa (or a point on the reference axis $A_{sb}$) and the irradiation point P. An arbitrary point in the three-dimensional space can uniquely be represented by the foregoing three information items. In this regard, however, it is required to preliminarily determine the reference points CPa and CPb in accordance with the arrangement of the scanning electromagnet 1*a* and 1*b*.

Here, it is assumed that the isocenter, which is an irradiation reference, is utilized as the origin of the xyz coordinate system, and the xyz coordinates of the reference point CPa and the xyz coordinates of the reference point CPb are given as follows.

reference point CPa: $(0, 0, -1_a)$ reference point CPb: $(0, 0, -1_b)$

Then, it is assumed that as illustrated in FIGS. 1 through 3, the upstream scanning electromagnets 1*a* and the downstream scanning electromagnet 1*b* are the x-direction scanning electromagnet and the y-direction scanning electromagnet, respectively. In this situation, when the coordinates of a certain point is given by $[\phi_a, \phi_b, r_b]$ represented by use of the special coordinate system described in the definition (D1), the x coordinate, the y coordinate, and the z coordinate of this certain point are given by the following equation (6).

$$\begin{bmatrix} x \\ y \\ z \end{bmatrix} = Rot_x(\varphi_b)\left\{ Rot_y(\varphi_a)\begin{bmatrix} 0 \\ 0 \\ l_a - l_b + r_b \end{bmatrix} - \begin{bmatrix} 0 \\ 0 \\ l_a - l_b \end{bmatrix} \right\} - \begin{bmatrix} 0 \\ 0 \\ l_b \end{bmatrix} \tag{6}$$

Here, when $Rot_x(\phi_b)$, and $Rot_y(\phi_a)$ in the equation (6) are defined as in (D2), the xyz coordinates of this certain point is obtained as in the equation (7).

$$Rot_x(\varphi_b) = \begin{bmatrix} 1 & 0 & 0 \\ 0 & \cos\varphi_b & -\sin\varphi_b \\ 0 & \sin\varphi_b & \cos\varphi_b \end{bmatrix},\ Rot_y(\varphi_a) = \begin{bmatrix} \cos\varphi_a & 0 & \sin\varphi_a \\ 0 & 1 & 0 \\ -\sin\varphi_a & 0 & \cos\varphi_a \end{bmatrix} \tag{D2}$$

$$\begin{aligned} \begin{bmatrix} x \\ y \\ z \end{bmatrix} &= Rot_x(\varphi_b)\left\{ \begin{bmatrix} (l_a - l_b + r_b)\sin(\varphi_a) \\ 0 \\ (l_a + l_b + r_b)\cos(\varphi_a) \end{bmatrix} - \begin{bmatrix} 0 \\ 0 \\ l_a - l_b \end{bmatrix} \right\} - \begin{bmatrix} 0 \\ 0 \\ l_b \end{bmatrix} \\ &= \begin{bmatrix} (l_a - l_b + r_b)\sin(\varphi_a) \\ -\sin(\varphi_b)\{(l_a - l_b + r_b)\cos(\varphi_a) - (l_a - l_b)\} \\ \cos(\varphi_b)\{(l_a - l_b + r_b)\cos(\varphi_a) - (l_a - l_b)\} \end{bmatrix} - \begin{bmatrix} 0 \\ 0 \\ l_b \end{bmatrix} \\ &= \begin{bmatrix} (l_a - l_b + r_b)\sin(\varphi_a) \\ -\sin(\varphi_b)\{(l_a - l_b + r_b)\cos(\varphi_a) - (l_a - l_b)\} \\ \cos(\varphi_b)\{(l_a - l_b + r_b)\cos(\varphi_a) - (l_a - l_b)\} - l_b \end{bmatrix} \end{aligned} \tag{7}$$

On the contrary, the method of obtaining the special coordinate system from the xyz coordinate system is described below.

Because $1_b$ is a given value that is inherent to an irradiation system, $\phi_b$ can be obtained, as in the equation (8), from the relationship between y and z in the equation (7).

$$\begin{aligned} \frac{-y}{z + l_b} &= \frac{\sin\varphi_b}{\cos\varphi_b} = \tan\varphi_b \\ \therefore\ \varphi_b &= \arctan\left(\frac{-y}{z + l_b}\right) \end{aligned} \tag{8}$$

Because being also a given value that is inherent to an irradiation system, $1_a$ can be defined, as in the definition (D3), from the relationship between y and z in the equation (7); thus, from the relationship with z in the equation (7) and the definition (D3), $\phi_a$ can be obtained from the equation (9).

$$\begin{aligned} \Lambda &:= y^2 + (z + l_b)^2 + (l_a - l_b) \\ &= (l_a - l_b + r_b)\cos\varphi_a \end{aligned} \tag{D3}$$

$$\begin{aligned} \frac{x}{\Lambda} &= \frac{\sin\varphi_a}{\cos\varphi_a} = \tan\varphi_a \\ \therefore\ \varphi_a &= \arctan\left(\frac{x}{\Lambda}\right) \end{aligned} \tag{9}$$

Lastly, $r_b$ can be obtained from the equation (10).

$$x^2 + \Lambda^2 = (l_a - l_b + r_b)^2$$

$$\therefore r_b = \sqrt{x^2 + \Lambda^2} - (l_a - l_b) \tag{10}$$

There is provided a coordinate transformation function in which the coordinate system $[\phi_a, \phi_b, r_b]$ conforming to the foregoing series-of-scanners beam spread is utilized already from the stage of Function a, i.e., as Function a or as an auxiliary function for implementing Function a, there is performed transformation to a special coordinate system, under the assumption of series-of-scanners.

Figure 10:
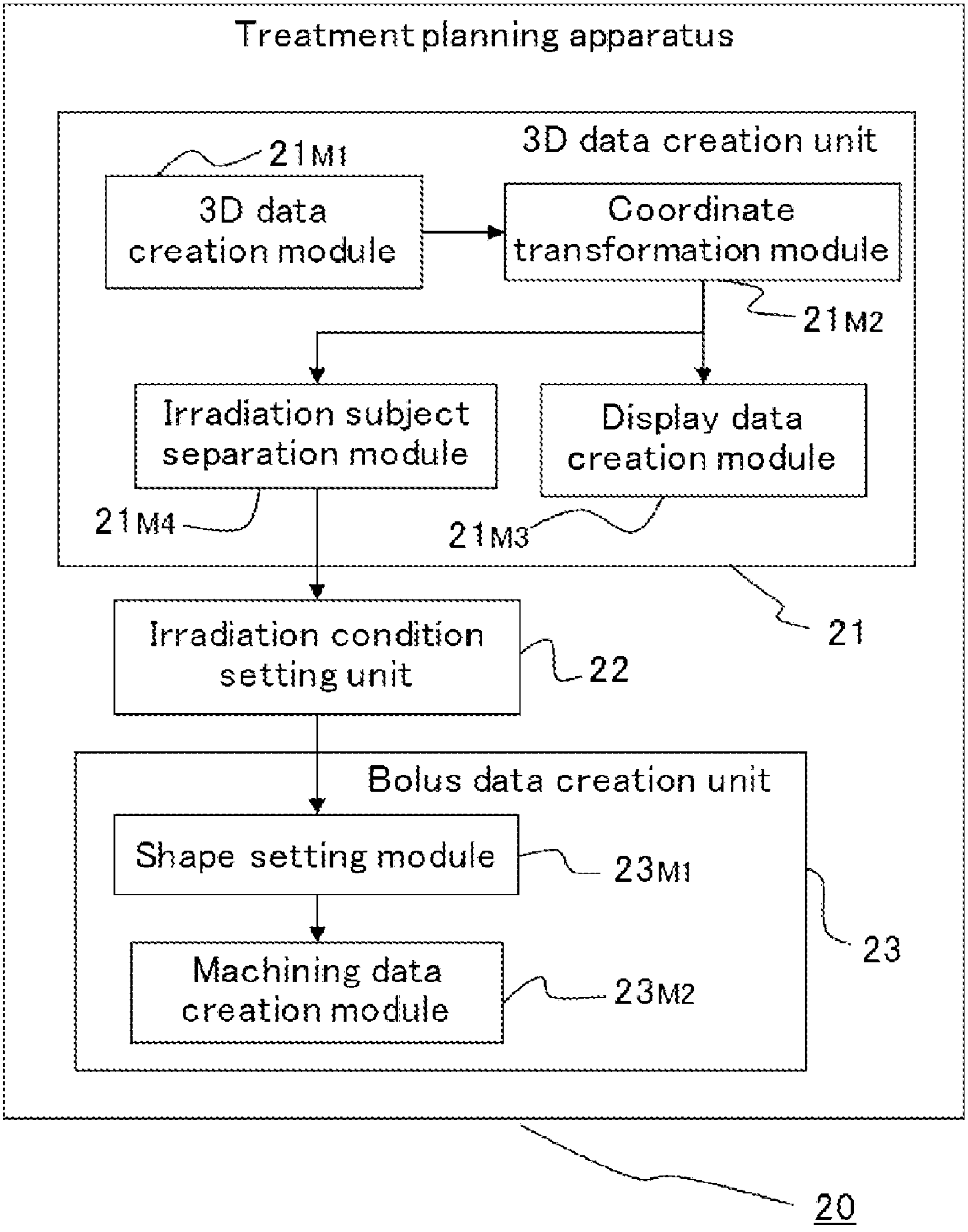
FIG. 10 is a block diagram for explaining the configuration of a treatment planning apparatus according to Embodiment 6 of the present invention.

For example, FIG. 10 illustrates, with a block diagram, the characteristic parts in the roles (units) and the functions (modules) of a treatment planning apparatus according to Embodiment 6 of the present invention. In FIG. 10, a treatment planning apparatus 20 is provided with a three-dimensional data creation unit 21 for creating three-dimensional data from image data on a diseased site, which is an irradiation subject; an irradiation condition setting unit 22 for setting an irradiation condition, based on the created three-dimensional data; and a bolus data creation unit 23 for creating bolus shape data and machining data for manufacturing, based on the set irradiation condition. As described above, these units and modules are formed in a computer by software; thus, these parts are not physically formed.

The three-dimensional data creation unit 21 is provided with a three-dimensional data creation module $\mathbf{21}_{M1}$ for, as Function a, creating three-dimensional data on a diseased site, a body shape, and the like; a coordinate transformation module $\mathbf{21}_{M2}$ for transforming the created three-dimensional data into data in the coordinate system $[\phi_a, \phi_b, r_b]$ represented through the definition (D1) under the assumption of series-of-scanners; a display data creation module $\mathbf{21}_{M3}$ for, as Function b, creating display data, based on the transformed data; and an irradiation subject separation module $\mathbf{21}_{M4}$ for distinguishing a diseased site, which is an irradiation subject, from normal tissues, based on the transformed data. As Role A, the three-dimensional data creation unit 21 creates, from image information, three-dimensional data in the coordinate system represented through the definition (D1).

As Functions d and e of Role B, the irradiation condition setting unit 22 sets an optimum irradiation condition, based on three-dimensional data in the coordinate system represented through the definition (D1). In order to realize Function g of Role D, the bolus data creation unit 23 is provided with at least a shape setting module $\mathbf{23}_{M1}$ that sets, based on the set irradiation condition, the shape of a bolus (path-length distribution data) in such a way that the sum of the depth $L_K$ of the diseased site IS and the path length $L_B$ through the bolus 6 satisfies the equation (2); and a machining data creation module $\mathbf{23}_{M2}$ that creates bolus machining data, based on the set shape.

Accordingly, in the three-dimensional data creation unit and the irradiation condition setting unit 22, the three-dimensional data in the coordinate system, represented through the definition (D1), for determining the irradiation position is specified by utilizing at least a beam deflection angle $\alpha(\phi_a)$ with respect to the reference axis ($A_{sa}$) that is perpendicular to the beam axis $X_B$ and passes through the reference point CPa, a beam deflection angle $\beta(\phi_b)$ with respect to the reference axis ($A_{sb}$) that is perpendicular to the beam axis $X_B$ and the reference axis $A_{sa}$ and passes through the reference point CPb, and the distance $r_b$.

Thus, the path length $L_K$, in the equation (2), between the body surface $f_K$ and the desired irradiation position P is obtained as the difference between the value $r_b$ of the body surface $f_k$ and the value $r_b$ of the desired irradiation position P with respect to the same values of α and β. Similarly, the penetration path length $L_B$ of a bolus is obtained as the difference between the value $r_b$ of the incident surface of the bolus and the value $r_b$ of the emitting side of the bolus with respect to the same values of α and β. In the case where there is utilized a machining apparatus whose axis angle can be changed, machining data is obtained by setting the cutting depth in accordance with the distribution of the bolus path length $L_B$ with respect to α and β.

In other words, in the case of the treatment planning apparatus 20 according to Embodiment 6 of the present invention, by directly utilizing the three-dimensional data inputted and outputted in the treatment planning apparatus 20, there can be created machining data for manufacturing a bolus for a particle beam therapy system utilizing the bolus 6 or 206 that accurately compensates the depth distribution for an irradiation system in which a particle beam spreads in a series-of-scanners manner. In the case where it is required to describe the machining data with the depth distribution, the machining data is transformed into the x, y, z coordinates and based on the x, y, z coordinates, there are set cutting depths, in the machining data, in accordance with the depths t (in the z direction) corresponding to x and y.

In the case where the foregoing coordinate system is utilized, also with regard to a driving code related to the multileaf collimator 5, the opening shape (penetration shape SP) itself conforming to the optimum irradiation plan obtained by the irradiation condition setting unit 22 becomes a driving code for realizing the shape. Accordingly, in an irradiation system in which a beam spreads in a series-of-scanners manner, a driving code for optimally controlling the multileaf collimator 5 can readily be created, as well.

As described above, the treatment planning apparatus 20 according to Embodiment 6 is provided with the three-dimensional data creation unit 21 for creating three-dimensional data from image data of a body including the to-be-irradiated portion IS; the irradiation condition setting unit 22 for setting an irradiation condition, based on the created three-dimensional data; and the bolus data creation unit 23 for creating the shape data on the bolus 6 in a particle beam therapy system according to each of foregoing embodiments, based on the set irradiation condition. The three-dimensional data creation unit 21 is configured in such a way as to create the three-dimensional data by utilizing at least the first slant α obtained by means of scanning of the upstream electromagnet 1*a* and the second slant β obtained by means of scanning of the other electromagnet 1*b*. In other words, three-dimensional data creation unit 21 is configured in such a way as to create the three-dimensional data by utilizing the beam deflection angle $\phi_a$ with respect to the reference axis $A_{sa}$ that is perpendicular to the beam axis $X_B$ and passes through the reference point CPa, and the beam deflection angle $\phi_b$ with respect to the reference axis $A_{sb}$ that is perpendicular to the beam axis $X_B$ and the reference axis $A_{sa}$ and passes through the reference point CPb. Therefore, there can be created the shape data and the machining data on a bolus for accurately compensating the depth of a diseased site, which is an irradiation subject, by directly utilizing three-dimensional data inputted and outputted in the treatment planning apparatus 20. That is to say, in the bolus data creation unit 23, the foregoing control data can be specified by two deflection angles $\phi_a$ and $\phi_b$ and the distance $r_b$; therefore, in an irradiation system in which a particle beam spreads in a series-of-scanners manner, there can be performed irradiation with a charged particle beam B formed into an accurate irradiation field only by the simple difference of the distance $r_b$ for the combination of the values $\phi_a$ and $\phi_b$.

DESCRIPTION OF REFERENCE NUMERALS

1: irradiation nozzle (1*a*: x-direction (upstream) scanning electromagnet, 1*b*: y-direction (downstream) scanning electromagnet)

2: ridge filter

3: range shifter

4: ring collimator

5: multileaf collimator

6: bolus

10: particle beam therapy system

20: treatment planning apparatus

21: three-dimensional data creation unit

22: irradiation condition setting unit

23: bolus data creation unit $A_{sa}$: scanning axis (1st axis) of upstream scanning electromagnet ($E_{As}$: virtual axis)

$A_{sb}$, scanning axis (2nd axis) of downstream scanning electromagnet

CPa: 1st reference point

CPb: 2nd reference point $F_B$: beam bundle (spread) of particle beam $L_B$: inner-bolus path length $L_K$: inner-body path length (inner-body depth) up to to-be-irradiated portion PS: penetration shape R: attainable depth ST: scanning locus of particle beam $T_B$: irradiation orbit $X_B$: beam axis of particle beam ($E_x$: beam axis of a beam entering bolus)

α: 1st slant

β: 2nd slant

Three-digit numbers each denotes a variant example in Embodiment.

The invention claimed is:

1. A bolus that is disposed in a particle beam therapy system and modulates energy distribution of a particle beam in accordance with a to-be-irradiated portion, wherein the shape of the bolus is set in such a way that, when a first reference point and a second reference point, which is at the downstream side of the first reference point, are given on a beam axis of a particle beam that enters the bolus at the upstream side thereof, and when an irradiation orbit of a particle beam that penetrates the bolus and reaches the to-be-irradiated portion is defined by a first slant from the beam axis with respect to a first axis that starts from the first reference point, that is perpendicular to the beam axis, and that includes the first reference point and by a second slant from the beam axis with respect to a second axis that is perpendicular to the beam axis and the first axis and includes the second reference point, a path length within the bolus of a particle beam in each of the irradiation orbits defined for combinations within a predetermined range of combinations of the first slant and the second slant, compensates a path length from a body surface situated at the upstream side of the to-be-irradiated portion to the to-be-irradiated portion.

2. The bolus according to claim 1, wherein the shape of the bolus is set in such a way that the following relationship is satisfied:

$$L_B(\alpha, \beta)+L_K(\alpha, \beta)=R$$

where

α denotes the first slant,

β denotes the second slant, $L_B(\alpha, \beta)$ denotes the path length, of a particle beam, within the bolus in an irradiation orbit defined by a combination of the first slant and the second slant, $L_K(\alpha, \beta)$ denotes the path length from the body surface to the to-be-irradiated portion in the irradiation orbit defined by the combination of the first slant and the second slant, and R denotes the attainable depth corresponding to the energy of a particle beam that enters the bolus, respectively.

3. A bolus manufacturing method for manufacturing the bolus according to claim 2, comprising the steps of:

acquiring inner-body depth data, which is the path length from the body surface to the to-be-irradiated portion, for each of combinations of the first slant and the second slant;

setting the shape of a bolus in such a way that the path length is obtained by compensating the acquired inner-body depth data;

creating bolus machining data, based on the set bolus shape; and machining a bolus, based on the created machining data.

4. A particle beam therapy system comprising:

an irradiation nozzle that scans a particle beam supplied from an accelerator by means of two electromagnets that range in the traveling direction of the particle beam and whose scanning directions are different from each other, and that irradiates the particle beam in such a way as to enlarge the irradiation field thereof; and the bolus according to claim 2, disposed in a particle beam irradiated from the irradiation nozzle, wherein the bolus is disposed in such a way that the first axis for setting the shape of the bolus coincides with the scanning axis of the upstream electromagnet out of the two electromagnets and the second axis coincides with the scanning axis of the other electromagnet.

5. The particle beam therapy system according to claim 4, wherein the irradiation nozzle enlarges the irradiation field utilizing a spiral wobbling method.

6. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 5, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

7. The particle beam therapy system according to claim 4, wherein the irradiation nozzle enlarges the irradiation field utilizing a scanning method.

8. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 7, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

9. The particle beam therapy system according to claim 4, wherein scanning for one direction out of the two directions is performed by a deflection electromagnet that deflects the direction of a beam axis, and by regarding that the scanning axis of the deflection electromagnet passes through a point on the beam axis of a particle beam that enters the bolus, the scanning axis of the deflection electromagnet is made to coincide with the first axis or the second axis.

10. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 9, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

11. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 4, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

12. A bolus manufacturing method for manufacturing the bolus according to claim 1, comprising the steps of:

acquiring inner-body depth data, which is the path length from the body surface to the to-be-irradiated portion, for each of combinations of the first slant and the second slant;

setting the shape of a bolus in such a way that the path length is obtained by compensating the acquired inner-body depth data;

creating bolus machining data, based on the set bolus shape; and machining a bolus, based on the created machining data.

13. A particle beam therapy system comprising:

an irradiation nozzle that scans a particle beam supplied from an accelerator by means of two electromagnets that range in the traveling direction of the particle beam and whose scanning directions are different from each other, and that irradiates the particle beam in such a way as to enlarge the irradiation field thereof; and the bolus according to claim 1, disposed in a particle beam irradiated from the irradiation nozzle, wherein the bolus is disposed in such a way that the first axis for setting the shape of the bolus coincides with the scanning axis of the upstream electromagnet out of the two electromagnets and the second axis coincides with the scanning axis of the other electromagnet.

14. The particle beam therapy system according to claim 13, wherein the irradiation nozzle enlarges the irradiation field utilizing a spiral wobbling method.

15. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 14, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

16. The particle beam therapy system according to claim 13, wherein the irradiation nozzle enlarges the irradiation field utilizing a scanning method.

17. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 16, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

18. The particle beam therapy system according to claim 13, wherein scanning for one direction out of the two directions is performed by a deflection electromagnet that deflects the direction of a beam axis, and by regarding that the scanning axis of the deflection electromagnet passes through a point on the beam axis of a particle beam that enters the bolus, the scanning axis of the deflection electromagnet is made to coincide with the first axis or the second axis.

19. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 18, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

20. A treatment planning apparatus comprising:

a three-dimensional data creation unit for creating three-dimensional data from image data of a body including the to-be-irradiated portion;

an irradiation condition setting unit for setting an irradiation condition, based on the created three-dimensional data; and a bolus data creation unit for creating shape data on a bolus in the particle beam therapy system according to claim 13, based on the set irradiation condition, wherein the three-dimensional data creation unit creates the three-dimensional data by utilizing at least the first slant corresponding to beam deflection angle by the upstream electromagnet and the second slant corresponding to beam deflection angle by said the other electromagnet.

* * * * *